(12) United States Patent
Arnott et al.

(10) Patent No.: US 8,754,240 B2
(45) Date of Patent: Jun. 17, 2014

(54) PROCESS FOR THE MANUFACTURE OF 4-FLUORO-2-METHYL-1H-INDOL-5-OL

(75) Inventors: Euan Alexander Arnott, Macclesfield (GB); John Crosby, Macclesfield (GB); Mathew Charles Evans, Macclesfield (GB); James Gair Ford, Macclesfield (GB); Martin Francis Jones, Macclesfield (GB); Kevin William Leslie, Macclesfield (GB); Ian Michael McFarlane, Macclesfield (GB); George Joseph Sependa, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/948,310

(22) Filed: Nov. 17, 2010

(65) Prior Publication Data

US 2011/0257395 A1    Oct. 20, 2011

Related U.S. Application Data

(62) Division of application No. 11/931,599, filed on Oct. 31, 2007, now Pat. No. 7,851,623.

(60) Provisional application No. 60/864,036, filed on Nov. 2, 2006, provisional application No. 60/957,401, filed on Aug. 22, 2007.

(51) Int. Cl.
   *C07D 209/04* (2006.01)

(52) U.S. Cl.
   USPC ......................................................... 548/508

(58) Field of Classification Search
   USPC ......................................................... 548/508
   See application file for complete search history.

(56) References Cited

U.S. PATENT DOCUMENTS

| | | |
|---|---|---|
| 5,962,458 A | 10/1999 | Lohmann et al. |
| 2003/0220357 A1 | 11/2003 | Bankston et al. |

FOREIGN PATENT DOCUMENTS

| | | |
|---|---|---|
| JP | 2004-269805 | 9/2004 |
| JP | 2005/347176 A | 12/2005 |
| JP | 2006-024785 | 1/2006 |
| WO | WO 95/15758 | 6/1995 |
| WO | WO 95/97137 | 10/1995 |
| WO | 96/33980 A | 10/1996 |
| WO | WO 00/47212 | 8/2000 |
| WO | WO 02/12227 | 2/2002 |
| WO | WO 03/064413 | 8/2003 |
| WO | WO 2004/009542 | 1/2004 |
| WO | 2004/046101 A2 | 6/2004 |
| WO | WO 2005/061488 | 7/2005 |
| WO | 2005/097137 A2 | 10/2005 |

OTHER PUBLICATIONS

Sorbera et al. "Cediranib. VEGFR inhibitor, Antiangiogenic agent, Oncolytic" Drugs of the future 32(7): 577-589 (2007).

Doherty et al. "Synthesis of Aminoisothiuronium salts and their conversion to mercaptoalkylguanidines and thiazolines" Journal of the American Chemical Society 79: 5667-5671 (1957).

European Search Report issued in related European Patent Application No. 12175034.3 dated Oct. 1, 2013.

*Primary Examiner* — Douglas M Willis

(74) *Attorney, Agent, or Firm* — Morgan, Lewis & Bockius LLP

(57) ABSTRACT

The present invention relates to a chemical process for the manufacture of a compound of Formula II

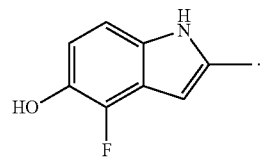

II

13 Claims, No Drawings

PROCESS FOR THE MANUFACTURE OF 4-FLUORO-2-METHYL-1H-INDOL-5-OL

This application is a Divisional application of U.S. patent application Ser. No. 11/931,599, filed Oct. 31, 2007 (now U.S. Pat. No. 7,851,623), which claims the benefit under 35 U.S.C. §119(e) of Application No. 60/864,036 filed 2 Nov. 2006 and Application No. U.S. 60/957,401, filed on 22 Aug. 2007. The present invention relates to chemical processes for the manufacture of certain quinazoline derivatives, or pharmaceutically acceptable salts thereof. The invention also relates to processes for the manufacture of certain intermediates useful in the manufacture of the quinazoline derivatives and to processes for the manufacture of the quinazoline derivatives utilising said intermediates.

In particular, the present invention relates to chemical processes and intermediates useful in the manufacture of the compound 4-(4-fluoro-2-methylindol-1H-5-yloxy)-6-methoxy-7-[3-(pyrrolidin-1-yl)propoxy]quinazoline. This compound falls within the disclosure of WO 00/47212 and is exemplified in Example 240 therein.

The compound 4-(4-fluoro-2-methylindol-1H-5-yloxy)-6-methoxy-7-[3-(pyrrolidin-1-yl)propoxy]quinazoline is described herein by way of the Formula I:

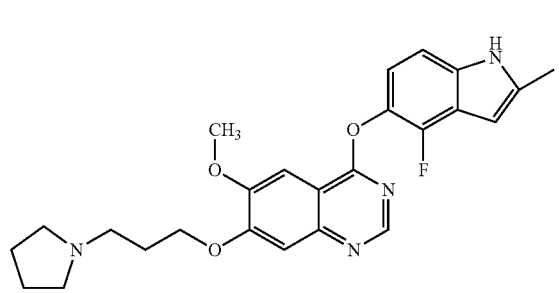

I and as AZD2171, the code number by which the compound is known.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57-66; Folkman, 1995, Nature Medicine 1: 27-31). Alteration of vascular permeability is thought to play a role in both normal and pathological physiological processes (Cullinan-Bove et al, 1993, Endocrinology 133: 829-837; Senger et al, 1993, Cancer and Metastasis Reviews, 12: 303-324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Antagonism of VEGF action by sequestration of VEGF with antibody can result in inhibition of tumour growth (Kim et al, 1993, Nature 362: 841-844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt-1 (also referred to as VEGFR-1), the kinase insert domain-containing receptor, KDR (also referred to as VEGFR-2 or Flk-1), and another fms-like tyrosine kinase receptor, Flt-4. Two of these related RTKs, Flt-1 and KDR, have been shown to bind VEGF with high affinity (De Vries et al, 1992, Science 255: 989-991; Terman et al, 1992, Biochem. Biophys. Res. Comm 1992, 187: 1579-1586). Binding of VEGF to these receptors expressed in heterologous cells has been associated with changes in the tyrosine phosphorylation status of cellular proteins and calcium fluxes.

VEGF is a key stimulus for vasculogenesis and angiogenesis. This cytokine induces a vascular sprouting phenotype by inducing endothelial cell proliferation, protease expression and migration, and subsequent organisation of cells to form a capillary tube (Keck et al, Science (Washington D.C.), 246: 1309-1312, 1989; Lamoreaux et al, Microvasc. Res., 55: 29-42, 1998; Pepper et al, Enzyme Protein, 49: 138-162, 1996). In addition, VEGF induces significant vascular permeability (Dvorak et al, Int. Arch. Allergy Immunol., 107: 233-235, 1995; Bates et al, Physiol. (Lond.), 533: 263-272, 2001), promoting formation of a hyper-permeable, immature vascular network which is characteristic of pathological angiogenesis.

It has been shown that activation of KDR alone is sufficient to promote all of the major phenotypic responses to VEGF, including endothelial cell proliferation, migration, and survival, and the induction of vascular permeability (Meyer et al, EMBO J., 18: 363-374, 1999; Zeng et al, J. Biol. Chem., 276: 32714-32719, 2001; Gille et al, J. Biol. Chem., 276: 3222-3230, 2001).

Angiogenesis and/or an increase in vascular permeability is present in a wide range of disease states including cancer (including leukaemia, multiple myeloma and lymphoma), diabetes, psoriasis, rheumatoid arthritis, Kaposi's sarcoma, haemangioma, acute and chronic nephropathies, atheroma, arterial restenosis, autoimmune diseases, asthma, acute inflammation, excessive scar formation and adhesions, lymphoedema, endometriosis, dysfunctional uterine bleeding and ocular diseases with retinal vessel proliferation including age-related macular degeneration.

AZD2171 is a potent inhibitor of VEGF RTK and demonstrates >800-5000 fold selectively compared to VEGFR-2 compared to the epidermal growth factor receptor tyrosine kinase, the ErbB2 receptor tyrosine kinase, the TEK (Tie-2) receptor tyrosine kinase and cyclin dependent kinase-2. AZD2171 shows excellent activity in the in vitro (a) enzyme and (b) HUVEC assays that are described in WO 00/47212 (pages 80-83). The AZD2171 $IC_{50}$ values for inhibition of isolated KDR (VEGFR-2), Flt-1 (VEGFR-1) and Flt-4 (VEGFR-3) tyrosine kinase activities in the enzyme assay were <2 nM, 5±2 nM and ≤3 nM respectively. AZD2171 inhibits VEGF-stimulated endothelial cell proliferation potently ($IC_{50}$ value of 0.4±0.2 nM in the HUVEC assay), but does not inhibit basal endothelial cell proliferation appreciably at a >1250 fold greater concentration ($IC_{50}$ value is >500 nM). The growth of a Calu-6 tumour xenograft in the in vivo solid tumour model described in WO 00/47212 (page 83) was inhibited by 49%, 69%* and 91%* following 28 days of once-daily oral treatment with 1.5, 3 and 6 mg/kg/day AZD2171 respectively (P<0.01, P***<0.0001; one-tailed t test). AZD2171 has been shown to elicit broad-spectrum antitumour activity in a range of models following once-daily oral administration (Wedge et al (2005) Cancer Research 65(10), 4389-4440).

WO 02/12227 discloses several possible routes for preparing indoleoxy bicyclic compounds. However, there is no specific disclosure in WO 02/12227 of a process for preparing a compound of the Formula I.

WO 00/47212 discloses a route for the preparation of a compound of Formula I (see Example 240). This route for preparing the compound of the Formula I is satisfactory for the synthesis of relatively small amounts of the compound. However, the route involves linear rather than convergent synthesis, requiring the use of multiple purification steps and the isolation of a substantial number of intermediates. As such, the overall yield of the synthesis is not high. There is, therefore, a need for a more efficient synthesis of the compound of the Formula I suitable to make larger quantities of that compound. There is also a need for more efficient syntheses of the intermediate compounds useful in the synthesis of the compound of the Formula I to make larger quantities of those intermediate compounds.

Preferably, the new syntheses should minimise the number of intermediate compounds that need to be isolated and should not involve costly and time-consuming purification procedures. Additionally, the new syntheses should form consistently high quality compounds, in particular so as to form a high quality compound of the Formula I to satisfy the high purity requirements of a pharmaceutical product. The new syntheses should also use procedures and reagents that can safely be used in a manufacturing plant and that meet environmental guidelines.

According to the present invention, we now provide improved processes for the manufacture of AZD2171, the compound of the Formula I.

According to the present invention, processes are also provided for the manufacture of key intermediate compounds that may be used in the manufacture of AZD2171.

The new processes are advantageous in that they allow the compounds to be made in high quality and high yield on a larger scale. The processes allow a substantial reduction in the number of intermediate compounds that must be isolated and, in general, are more convergent than the previous routes. Such changes provide significant advantages of time and cost.

For the avoidance of doubt, the term "AZD2171" as used hereinafter refers to the AZD2171 free base, unless otherwise stated.

A key intermediate that may be used in the preparation of AZD2171 is 2-methyl-4-fluoro-5-hydroxy-indole, the compound of the Formula II:

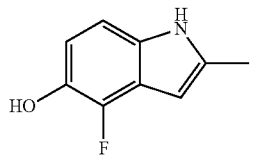

Example 237 of WO 00/47212 discloses three routes for the preparation of a compound of the Formula II.

(i) The first route involves the reaction of 2-fluoro-4-nitroanisole with 4-chlorophenoxyacetonitrile in dimethylformamide (DMF) solvent in the presence of potassium tert-butoxide followed by reduction with hydrogen using a palladium on charcoal catalyst to give a mixture of 4-fluoro-5-methoxyindole and 6-fluoro-5-methoxyindole. After protection of the indole nitrogen with tert-butoxycarbonyl, the mixture of protected indoles is reacted in tetrahydrofuran (THF) solvent with tert-butyllithium and methyl iodide followed by trifluoroacetic acid to give a mixture of 6-fluoro-5-methoxy-2-methyl-indole and 4-fluoro-5-methoxy-methylindole. After purification the 4-fluoro-5-methoxy-methylindole is reacted with boron tribromide in methylene chloride to give the compound of Formula II, 4-fluoro-5-hydroxy-2-methylindole.

(ii) The second route involves the reaction of ethyl acetoacetate with 1,2,3-trifluoro-4-nitrobenzene in THF in the presence of sodium hydride to form 3-acetylmethyl-1,2-difluoro-4-nitrobenzene. 3-Acetylmethyl-1,2-difluoro-4-nitrobenzene is then reacted with trimethyl orthoformate in methylene chloride in the presence of montmorillonite to form 1,2-difluoro-3-(2,2-dimethoxypropyl)-4-nitrobenzene. 1,2-Difluoro-3-(2,2-dimethoxypropyl)-4-nitrobenzene is then reacted with benzyl alcohol in dimethylacetamide (DMA) in the presence of sodium hydride to form 3-acetylmethyl-1-benzyloxy-2-fluoro-4-nitrobenzene. This compound is cyclized and deprotected by reacting with 10% palladium on charcoal in ethanol/acetic acid in the presence of hydrogen to give the compound of Formula II, 4-fluoro-5-hydroxy-2-methylindole.

(iii) The third route involves the reaction of 1,2-difluoro-3-(2,2-dimethoxypropyl)-4-nitrobenzene with sodium methoxide in methanol to give 3-acetylmethyl-2-fluoro-1-methoxy-4-nitrobenzene. This compound is cyclized and deprotected by reacting with titanium trichloride in acetone in the presence of ammonium acetate to give the 4-fluoro-5-methoxy-2-methylindole. The 4-fluoro-5-methoxy-methylindole is then reacted with boron tribromide in methylene chloride to give the compound of Formula II, 4-fluoro-5-hydroxy-2-methylindole.

The routes disclosed in the prior art documents for the preparation of a compound of the Formula II are satisfactory for the synthesis of relatively small amounts of the compound. However, they all require each of the intermediates to be isolated and, therefore, include multiple isolation and/or purification steps. This results in a satisfactory overall yield of the compound of the Formula II on the small scale used. However, the routes disclosed in the prior art documents are unsuitable for use on a manufacturing scale because they include multiple isolation and/or purification steps, which cannot be conducted efficiently on a manufacturing scale. In particular, the routes disclosed in the prior art documents are unsuitable for use in the manufacture of a high purity pharmaceutical product.

There is, therefore, a need for a more efficient synthesis of a compound of the Formula II suitable for use to make larger quantities of that compound. Preferably, the new synthesis should not involve costly and time-consuming isolation and/or purification procedures. Thus, the new synthesis should reduce the number of isolation and/or purification procedures required, thereby reducing costs and time of manufacture. Preferably, the new synthesis should minimise the number of solvents used throughout the process, which improves environmental performance and provides the opportunity for solvent recovery. Preferably, the new synthesis should also provide a robust and reliable method of isolating the compound of the Formula II and consistently should provide high quality compound of the Formula II, for example so as to satisfy the regulatory requirements for the introduction of starting materials into the production of pharmaceutical products.

International patent application, publication number WO 2004/009542 discloses an alternative method for making 2-methyl-4-fluoro-5-hydroxy-indole.

According to a first aspect of the present invention, there is provided a process for the manufacture of a compound of the Formula II from a nitrobenzene derivative of Formula III:

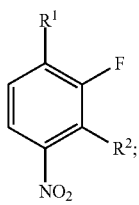

III wherein $R^1$ and $R^2$ are independently selected from fluorine, chlorine, bromine, iodine and optionally substituted alkylsulphonyloxy such as trifloxy or tosyloxy;

which process comprises the steps of:

(a) reacting a compound of Formula III with an ester of Formula (IV)

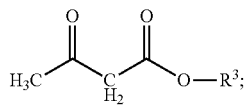

IV wherein $R^3$ is a suitable esterifying group;

to form a compound of the Formula V:

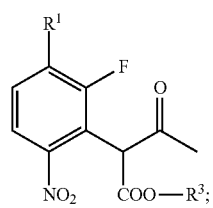

V (b) reacting a compound of Formula V with hydroxide ion in the presence of an aryl-alkyl ammonium salt or a tetraalkyl ammonium salt to form a compound of Formula VI

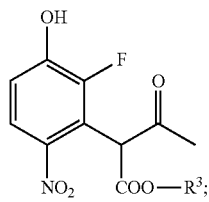

VI (c) reacting a compound of Formula VI to form a compound of Formula VII;

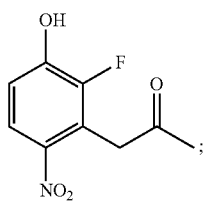

VII (d) reduction of the compound of the Formula VII to form a compound of Formula II.

In one embodiment $R^1$ and $R^2$ are independently selected from fluorine, chlorine, bromine and iodine. In another embodiment $R^1$ and $R^2$ are independently selected from fluorine, chlorine and bromine In another embodiment $R^1$ is fluorine and $R^2$ is bromine In another embodiment both $R^1$ and $R^2$ are fluorine.

$R^3$ is a suitable esterifying group such as optionally substituted $C_{1-6}$alkyl or optionally substituted benzyl. The skilled person would be able to select suitable esterifying groups which would not interfere with the processes of this embodiment of the invention and would allow removal of the ester group during process step (c).

In one embodiment $R^3$ is $C_{1-6}$alkyl or benzyl. In another embodiment $C_{1-6}$alkyl. In another embodiment $R^3$ is $C_{1-4}$alkyl. In a further embodiment $R^3$ is $C_4$alkyl, conveniently tert-butyl.

Reaction Conditions for Process (a)

The reaction of process (a) is conveniently carried out in the presence of a suitable solvent such as tetrahydrofuran or acetonitrile or in another embodiment a suitable non-polar solvent, such as toluene, trimethylbenzene or xylene, in the presence of a suitable base such as sodium t-butoxide or sodium tert-pentoxide. In another embodiment the non-polar solvent is selected from toluene or trimethylbenzene.

The reaction of step (a) is carried out at a temperature in the range, for example, of from 50 to 110° C., conveniently in the range of from 60 to 80° C., more conveniently in the range of from 65 to 75° C.

The compound of Formula IV may conveniently be selected from methyl 3-oxobutanoate, ethyl 3-oxobutanoate, propyl 3-oxobutanoate, butyl 3-oxobutanoate, sec-butyl 3-oxobutanoate and t-butyl 3-oxobutanoate. Alternatively the compound of Formula IV may be selected from methyl 3-oxobutanoate, ethyl 3-oxobutanoate and t-butyl 3-oxobutanoate. Conveniently t-butyl 3-oxobutanoate can be used since this requires milder reaction conditions to be used in the process which has the advantage that the reactions are easier to perform and lower levels of side products are produced.

Reaction Conditions for Process (b)

The reaction of process (b) is conveniently carried out in a suitable solvent such as water or a water miscible solvent such as tetrahydrofuran or acetonitrile in the presence of a suitable base such as sodium hydroxide, potassium hydroxide or lithium hydroxide.

The reaction of step (b) is carried out at a temperature in the range, for example, of from 30 to 70° C., conveniently in the range of from 40 to 60° C., more conveniently in the range of from 45 to 55° C.

Examples of aryl-alkyl ammonium salts include Triton B (trimethyl benzyl ammonium hydroxide) which is commercially available. Examples of tetra-alkyl ammonium salts include tetra-butyl ammonium chloride and tetra-butyl ammonium bromide.

Reaction Conditions for Process (c)

The reaction of process (c) is conveniently carried out in a suitable solvent, such as dichloromethane in the presence of an acid, such as trifluoroacetic acid or toluene in the presence of an acid, such as para-toluene sulphonic acid, acetic acid, propionic acid or a mixture of acetic acid and sulphuric acid.

When trifluoroacetic acid in dichloromethane is used the reaction of step (c) is carried out at a temperature in the range, for example, of from 0 to 40° C., conveniently in the range of from 10 to 35° C., more conveniently in the range of from 20 to 30° C. When toluene is used in the presence of para-toluene sulphonic acid, acetic acid, propionic acid or a mixture of acetic acid and sulphuric acid the reaction of step (c) is carried out a temperature in the range of between 80° C. and the boiling point of the solvent/acid mixture. In one embodiment the temperature is 90° C.

Reaction Conditions for Process (d)

The skilled practitioner will be familiar with a number of methods suitable for the reduction of a compound of Formula VII. For example sodium dithionite or hydrogen gas in the presence of a suitable catalyst such as palladium on charcoal. When sodium dithionite is used the reaction of process (d) is conveniently carried out in a suitable solvent such as water or a water miscible solvent such as tetrahydrofuran, acetonitrile or an alcohol for example methanol, ethanol or isopropanol advantageously in the presence of a suitable base such as potassium carbonate or sodium carbonate. For further examples the reader is referred to Comprehensive Organic Transformations" by Richard C. Larock, published by John Wiley and Sons, 2nd Edition which is incorporated herein by reference.

The reaction of step (d) is carried out at a temperature in the range, for example, of from 0 to 50° C., conveniently in the range of from 10 to 40° C., more conveniently in the range of from 20 to 30° C.

The process of the first aspect of the present invention is advantageous in that it allows a compound of the Formula II to be made in high quality and high yield on a larger scale.

The steps (a) to (c) can optionally be conducted as a continuous process without isolation and/or purification of the intermediate compounds of the Formulae V and VI. This significantly reduces the time and cost of manufacturing the compound of the Formula II on a larger scale.

In one aspect, the process for the manufacture of a compound of the Formula II may further include the step (e) of isolating and/or purifying the compound of the Formula II. The step (e) may comprise any suitable steps or procedures for isolating the desired product that are described in the literature and/or that are known to the skilled person. Particular steps that would be of use would provide high quality and high purity product.

The step (e) may, for example, also comprise crystallisation using a suitable solvent system. An example of a suitable solvent system is a solvent system comprising dissolving the product in dichloromethane and crystallisation by the addition of isohexane or isoheptane, which provides a compound of the Formula II in a high purity, typically in a purity of greater than 90%, conveniently greater than 98%.

In another aspect of the invention there is provided a compound of Formula VI or a salt thereof or a protected derivative thereof. Examples of protected derivatives include compounds wherein the hydroxy group is replaced by $C_{1-6}$alkoxy or aryloxy.

Another key intermediate that may be used in the preparation of AZD2171 is the compound of the Formula VIII:

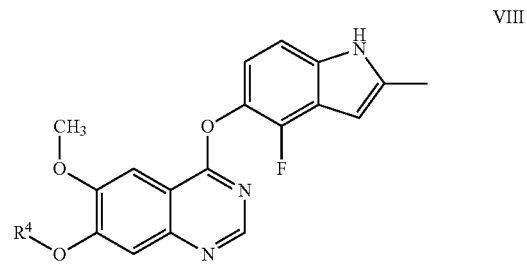

VIII wherein $R^4$ is a protecting group.

Example 7 of WO 03/064413 discloses a route for the preparation of a compound of the Formula VIII wherein $R^4$ is benzyl. The route involves the reaction of 7-benzyloxy-4-chloro-6-methoxyquinazoline free base with 4-fluoro-5-hydroxy-2-methylindole and potassium carbonate in a N-methyl pyrrolidinone as solvent to provide the compound of the Formula VIII. It is stated in Example 7 of WO 03/064413 that 7-benzyloxy-4-chloro-6-methoxyquinazoline was prepared from 7-benzyloxy-6-methoxy-3,4-dihydroquinazolin-4-one by reaction with thionyl chloride in dimethylformamide as solvent.

The routes disclosed in the prior art documents for the preparation of a compound of the Formula VIII are satisfactory for the synthesis of relatively small amounts of the compound. However, they all require the isolation and/or purification of intermediate compounds. This results in a satisfactory, but not high, overall yield of the compound of the Formula VIII.

There is, therefore, a need for a more efficient synthesis of a compound of the Formula VIII suitable for use to make larger quantities of that compound. Preferably, the new synthesis should not involve costly and time-consuming isolation and/or purification procedures. Thus, the new synthesis should reduce the number of isolation and/or purification procedures required, thereby reducing costs and time of manufacture. The new synthesis should conveniently also allow for effective isolation of the compound of the Formula VIII in a crystalline form in high purity and yield, which crystalline form should have good filtration characteristics.

According to a second aspect of the present invention, there is provided a process for the manufacture of a compound of the Formula VIII:

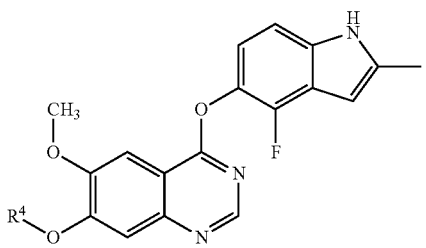

wherein R⁴ is a protecting group
from a compound of the Formula IX:

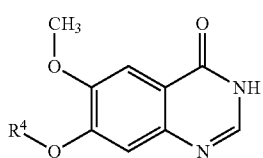

which process comprises the steps of:
(f) reaction of a compound of Formula IX with a derivatizing agent to form a compound of Formula X
wherein L¹ is a leaving group; and

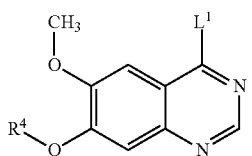

(g) reacting the compound of the Formula X with a compound of Formula II (2-methyl-4-fluoro-5-hydroxy-indole) optionally in situ and optionally in the presence of the solvent used in step (f) to form the compound of the Formula VIII.

The term 'protecting group' refers to groups which are readily removed under mild acidic conditions, neutral conditions or mild basic conditions. Suitable methods for protection are those known to those skilled in the art. Conventional protecting groups may be used in accordance with standard practice (for illustration see T. W. Green, Protective Groups in Organic Synthesis, John Wiley and Sons, 1991). Suitable protecting groups at R⁴ include benzyl, substituted benzyl (for example $C_{1-4}$alkoxybenzyl, di-alkoxybenzyl, alkylbenzyl and di-$C_{1-4}$alkybenzyl), tert-butyl, 1,1-dimethyl-1-ethylmethyl, allyl, substituted allyl (such as $C_{1-4}$alkylallyl) or methoxyethoxymethyl. In another embodiment R⁴ is benzyl.

For the avoidance of doubt the term 'in situ' means that the reaction was performed without isolation of the products from the previous process step.

The process of the second aspect of the invention is advantageous in that it allows a compound of the Formula VIII to be made in high purity and high yield on a larger scale.

The derivatizing agent could comprise any suitable agent for inserting a leaving group at the 4 position of the compound of Formula IX. Examples of L¹ include chlorine, bromine, iodine and optionally substituted alkylsulphonyl such as triflyl and tosyl. Examples of derivatizing agents include a chlorinating agent (such as phosphorus oxychloride), a brominating agent (such as phosphorus oxybromide or a mixture of N-bromosuccinimide and tri-isopropyl phosphite) and an iodinating agent.

When the derivatizing agent is a chlorinating, brominating or iodinating agent the process step (f) could comprise:
(f) reacting the compound of the Formula IX with a suitable derivatizing agent in the presence of a suitable base and a suitable solvent, wherein the reaction is carried out by:
(f-1) adding a mixture of the compound of the Formula IX and the base in the solvent to a mixture of the derivatizing agent in the solvent at a temperature in the range of from 60 to 110° C. over a period of about 60 minutes; or
(f-2) adding the derivatizing agent to a mixture of the compound of the Formula IX and the base in the solvent at ambient temperature over a period of about 15 minutes and then heating the reaction mixture over a period of about 90 minutes to a temperature in the range of from 70 to 90° C. and stirring the reaction mixture at that temperature for about 1 hour; or
(f-3) adding the derivatizing agent to a mixture of the compound of the Formula IX and the base in the solvent at a temperature in the range of from 60 to 110° C. over a period of about 15 minutes, A suitable solvent in step (f) is selected from toluene, chlorobenzene, 1,2-dimethoxyethane, acetonitrile and anisole. In one embodiment the solvent is anisole or toluene. In another embodiment the solvent is anisole.

A suitable solvent in step (g) is selected from toluene, chlorobenzene, 1,2-dimethoxyethane and anisole. In one embodiment the solvent is anisole or toluene. In another embodiment the solvent is anisole.

A co-solvent or co-solvents may be required to be added to solvents in (f) and (g) for example to aid solubility of the chlorobenzyline or indole intermediates. For example anisole can optionally comprise acetonitrile and N-methyl pyrolidinone and 1,2-dimethoxyethane can comprise N-methyl pyrolidinone.

In one aspect of the invention, steps (f) and (g) are conducted in toluene as the solvent.

In another aspect of the invention, steps (f) and (g) are conducted in anisole as the solvent.

The product of step (f) need not be isolated before conducting the step (g). This allows the process to be conducted as a continuous process without isolation and/or purification of the intermediate compound of the Formula X. This significantly reduces the time and cost of manufacturing the compound of the Formula VIII on a larger scale. The use of anisole as the reaction solvent is advantageous because this solvent minimise the formation of by-products. The choice of solvent also allows for the easy and convenient isolation of the compound of the Formula VIII. For example, when the reaction mixture is cooled to ambient temperature, the compound of the Formula VIII typically forms a solid, which solid may then be collected by any conventional method.

The mode of addition of the reagents in step (f) (i.e. as described in steps (f-1), (f-2) and (f-3)) is advantageous because it minimises the formation of by-products/impurities in that step. Reducing the formation of by-products/impurities enables the intermediate compound of the Formula X produced in step (f) to be used in step (g) without isolation and/or purification. Reducing the formation of by-products/impurities in step (f) also allows for the correct stoichiometry of the reagents in step (g) of the process and, therefore, a more efficient reaction in that step. This is turn provides a high yield and high purity of the compound of the Formula IX in step (g).

A suitable chlorinating agent for use in step (f) is phosphorus oxychloride. Typically, in step (f), a molar excess of chlorinating agent is used relative to the compound of the Formula IX. For example, a molar excess in the range of from 1 to 2.0, conveniently in the range of from 1.2 to 1.4, may be used.

A suitable base for use in step (f) is a base selected from triethylamine and N,N-diisopropylethylamine. In particular, the base is diisopropyethylamine. Adding a source of chloride to the reaction mixture (such as, for example, triethylamine hydrochloride) may reduce the formation of by-products.

In step (f-1), the reaction is carried out at a temperature in the range of from 60 to 80° C., conveniently in the range of from 65 to 75° C., more conveniently in the range of from 70 to 75° C.

In step (f-2), the addition of reagents is carried out at ambient temperature. By the term "ambient temperature" we mean a temperature in the range of from −10 to 30° C., especially a temperature in the range of from 10 to 20° C., more especially a temperature of about 15° C. The reaction mixture is then heated to a temperature in the range of from 70 to 90° C., conveniently in the range of from 75 to 85° C., more conveniently in the range of from 80 to 85° C.

In step (f-3), the reaction is carried out at a temperature in the range of from 70 to 90° C., conveniently in the range of from 75 to 85° C., more conveniently in the range of from 80 to 85° C.

In step (f), the term "of about" is used in the expressions "of about 60 minutes", "of about 15 minutes", "of about 90 minutes and "of about 1 hour" to indicate that the time periods quoted should not be construed as being absolute values because, as will be appreciated by those skilled in the art, the time periods may vary slightly. For example, the time periods quoted may vary by ±50%, particularly by ±15%, particularly by ±10% from the values quoted in step (f).

In one aspect of the invention, following step (f) of the process, the compound of the Formula X is isolated and/or purified, for example before storage, handling and/or further reaction. Therefore, in one aspect of the invention, the process for manufacturing a compound of the Formula X further includes the step of isolating the compound of the Formula X. The step may comprise any suitable steps or procedures for isolating the desired product that are described in the literature and/or that are known to the skilled person. Particular steps that would be of use would provide high quality and high purity product.

The reaction of step (g) is carried out at a temperature in the range of from 60 to 85° C., conveniently in the range of from 65 to 80° C., more conveniently in the range of from 70 to 75° C.

In one aspect of the invention, following step (g) of the process, the compound of the Formula VIII is isolated and/or purified, for example before storage, handling and/or further reaction. Therefore, in one aspect of the invention, the process for manufacturing a compound of the Formula VIII further includes the step (h) of isolating the compound of the Formula VIII. The step (h) may comprise any suitable steps or procedures for isolating the desired product that are described in the literature and/or that are known to the skilled person. Particular steps that would be of use would provide high quality and high purity product. The reaction mixture may be cooled to ambient temperature, at which temperature the compound of the Formula VIII typically forms a solid, and the solid so formed may be collected by any conventional method, for example by filtration.

Both the compounds of the Formula IX and the nitrobenzene derivative of Formula III starting material are commercially available or can be prepared using conventional methods. For example the compound of Formula IX may be prepared as described in Example 5, preparation of starting materials.

Another key intermediate that may be used in the preparation of AZD2171 is 7-hydroxy-4-(4-fluoro-2-methylindol-5-yloxy)-6-methoxyquinazoline, the compound of the Formula XI:

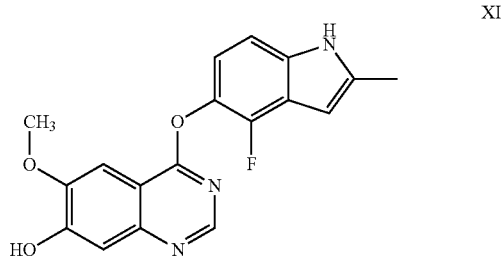 [SMILES: COc1cc2c(Oc3ccc4[nH]c(C)cc4c3F)ncnc2cc1O]

Example 7 of WO 03/064413 discloses a route for the preparation of a compound of the Formula XI. The route involves the reaction of 7-benzyloxy-4-(2-methyl-4-fluoroindol-5-yloxy)-6-methoxyquinazoline (a compound of Formula VIII) with ammonium formate in dimethylformamide containing 10% palladium on carbon to give a compound of Formula XI.

This route disclosed in the prior art for the preparation of a compound of the Formula XI is satisfactory for the synthesis of relatively small amounts of the compound. However, it requires the isolation and/or purification of intermediate compounds. This results in a satisfactory, but not high, overall yield of the compound of the Formula XI.

There is, therefore, a need for a more efficient synthesis of the compound of the Formula XI suitable for use to make larger quantities of that compound. Preferably, the new synthesis should not involve costly and time-consuming purification procedures. Thus, the new synthesis should reduce the number of isolation and/or purification procedures required, thereby reducing costs and time of manufacture. Preferably, the new synthesis should minimise the number of solvents used throughout the process, which improves environmental performance and provides the opportunity for solvent recovery. The new synthesis should also enable effective crystallisation of the compound of the Formula XI in a crystalline form with good filtration characteristics and in high purity and yield.

According to a third aspect of the present invention, there is provided a process for the manufacture of 7-hydroxy-4-(4-fluoro-2-methylindol-5-yloxy)-6-methoxyquinazoline, a compound of the Formula XI:

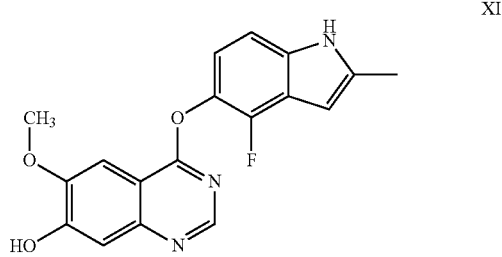 [SMILES: COc1cc2c(Oc3ccc4[nH]c(C)cc4c3F)ncnc2cc1O]

from a compound of the Formula IX:

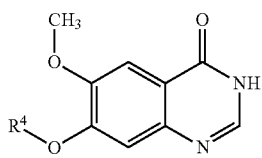

wherein R⁴ is a protecting group
which process comprises the steps of:
(f) reaction of a compound of Formula IX with a derivatizing agent to form a compound of Formula X
wherein L¹ is a leaving group;

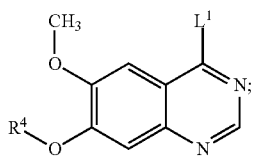

(g) reacting the compound of the Formula X with a compound of Formula II (2-methyl-4-fluoro-5-hydroxy-indole), optionally in situ, optionally in the presence of the solvent used in step (f) to form a compound of the Formula VIII;

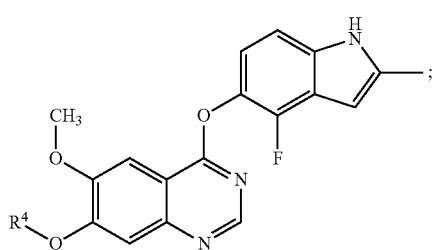

and
(i) removing R⁴ from the compound of the Formula VIII to form the compound of the Formula XI or a salt thereof;
and whereafter the compound of the Formula XI obtained in the form of the free base may be converted into a salt form and the compound of the Formula XI obtained in the form of a salt may be converted into the free base or into the form of an alternative salt, if necessary.

When the derivatizing agent is a chlorinating, brominating or iodinating agent the process step (f) could comprise:
(f) reacting the compound of the Formula IX with a suitable derivatizing agent in the presence of a suitable base and a suitable solvent, wherein the reaction is carried out by:
(f-1) adding a mixture of the compound of the Formula IX and the base in the solvent to a mixture of the derivatizing agent in the solvent at a temperature in the range of from 60 to 110° C. over a period of about 60 minutes; or
(f-2) adding the derivatizing agent to a mixture of the compound of the Formula IX and the base in the solvent at ambient temperature over a period of about 15 minutes and then heating the reaction mixture over a period of about 90 minutes to a temperature in the range of from 70 to 90° C. and stirring the reaction mixture at that temperature for about 1 hour; or
(f-3) adding the derivatizing agent to a mixture of the compound of the Formula IX and the base in the solvent at a temperature in the range of from 60 to 110° C. over a period of about 15 minutes, The process of the third aspect of the invention is advantageous in that it allows the compound of the Formula XI to be made in high purity and high yield on a larger scale.

Reaction Conditions for Process (i)

The reaction of step (i) is carried out at a temperature in the range of from 20 to 60° C., more conveniently in the range of from 35 to 45° C.

In one aspect of the invention the reduction of the compound of Formula VIII is performed by catalytic hydrogenation, for example using hydrogen gas and an appropriate catalyst such as palladium on carbon.

In another aspect of the invention the reduction of the compound of Formula VIII is performed by catalytic transfer hydrogenation, using for example a non-gaseous hydrogen donor such as cyclohexene or ammonium formate and an appropriate catalyst such as palladium on carbon.

Suitable solvents for step (i) include N-methylpyrrolidinone (NMP), dimethylformamide or dimethylacetamide.

In one aspect of the invention, following step (i) of the process, the compound of the Formula XI is isolated and/or purified. Any suitable steps or procedures for isolating and/or purifying the desired product that are described in the literature and/or that are known to the skilled person may be used. Particular steps that would be of use would provide high quality and high purity product. For example the compound of Formula XI may be isolated from NMP by addition of an antisolvent such as water, methanol, ethanol, isopropanol, butanol or acetonitrile.

In another embodiment of the invention, following the process (i), the compound of Formula XI is used in situ in the next step in the process.

According to a further embodiment of the third aspect of the invention there is provided a process for the manufacture of a compound of Formula XI from a compound of Formula X comprising the process steps (g) and (i) above.

According to a further embodiment of the third aspect of the invention there is provided a process for the manufacture of 7-hydroxy-4-(4-fluoro-2-methylindol-5-yloxy)-6-methoxyquinazoline, a compound of the Formula XI:

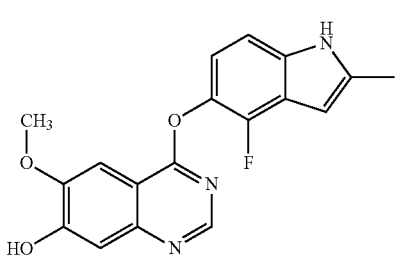

is from a compound of the Formula IX:

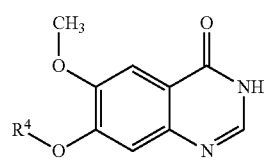

wherein R⁴ is a protecting group
which process comprises the steps of:
(f) reaction of a compound of Formula IX with a derivatizing agent to form a compound of Formula X
wherein L¹ is a leaving group;

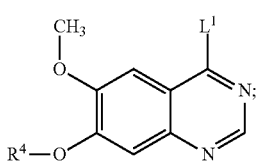

X (g-1) reacting the compound of the Formula X with a compound of Formula VII,

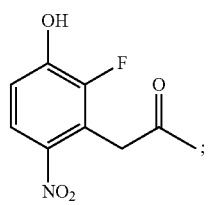

VII optionally in situ, optionally in the presence of the solvent used in step (f), to form the compound of the Formula XIV:

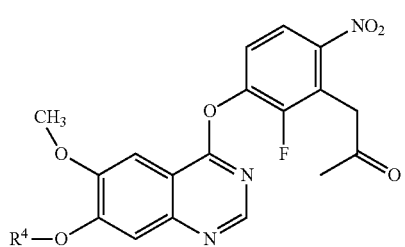

XIV (i-1) reducing a compound of Formula XIV to form a compound of Formula XI

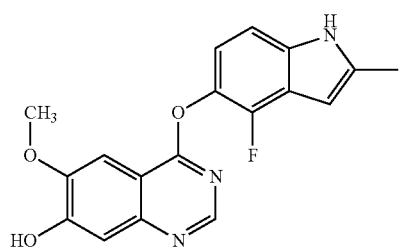

XI

Reaction Conditions for Process (f)

Reaction conditions for step (f) are as described above.

The derivatizing agent could comprise any suitable agent for inserting a leaving group at the 4 position of the compound of Formula IX. Examples of L¹ include chlorine, bromine, iodine and optionally substituted alkylsulphonyl such as triflyl and tosyl. Examples of derivatizing agents include a chlorinating agent (such as phosphorus oxychloride), a brominating agent (such as phosphorus oxybromide or a mixture of N-bromosuccinimide and tri-isopropyl phosphite) and an iodinating agent.

R⁴ is a protecting group as defined above.

Reaction Conditions for Process (g-1)

The reaction of step (g-1) is carried out by addition of a solution of a salt of a compound of the Formula VII to a solution of a compound of the Formula X in the solvent used in step (f-1). The salt of a compound of the Formula VII may be prepared by use of lithium hydroxide, potassium hydroxide, sodium hydroxide, lithium carbonate, potassium carbonate, sodium carbonate or cesium carbonate. Optimally sodium hydroxide is used. The salt is formed at a temperature of −20° C. to +20° C., more conveniently in the range −10° C. to 0° C. The solution of the salt of a compound of the Formula VII is added to a solution of a compound of the Formula X in the solvent used in step (f-1) at a temperature of 60° C. to 100° C., conveniently in the range 70-90° C.

Reaction Conditions for Process (i-1)

The reaction of step (i-1) is carried out at a temperature in the range of from 20 to 60° C., more conveniently in the range of from 35 to 45° C.

In one aspect of the invention the reduction of the compound of Formula XIV is performed by catalytic hydrogenation, for example using hydrogen gas and an appropriate catalyst such as palladium on carbon.

In another aspect of the invention the reduction of the compound of Formula XIV is performed by catalytic transfer hydrogenation, using for example a non-gaseous hydrogen donor such as cyclohexene or ammonium formate and an appropriate catalyst such as palladium on carbon.

Suitable solvents for step (i) include N-methylpyrrolidinone (NMP), dimethylformamide or dimethylacetamide.

In one aspect of the invention, following step (i-1) of the process, the compound of the Formula XI is isolated and/or purified. Any suitable steps or procedures for isolating and/or purifying the desired product that are described in the literature and/or that are known to the skilled person may be used. Particular steps that would be of use would provide high quality and high purity product. For example the compound of Formula XI may be isolated from NMP by addition of an antisolvent such as water, methanol, ethanol, isopropanol, butanol or acetonitrile.

In another embodiment of the invention, following the step (i-1), the compound of Formula XI is used in situ in the next step in the process.

According to a further embodiment of the third aspect of the invention there is provided a process for the manufacture of a compound of Formula XI from a compound of Formula X comprising the process steps (g-1) and (i-1) above.

In a further embodiment of the invention there is provided a compound of Formula XIV.

The further embodiment of the third aspect of the invention is applicable to the preparation of a number of ring systems substituted by 4-fluoro-2-methylindol-5-yloxy. Thus according to this further embodiment there is provided a process for the manufacture of a compound of Formula XI-1

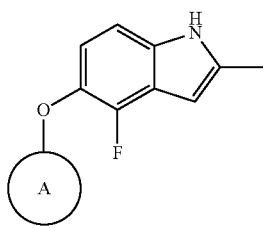

XI-1 wherein A is a suitable ring system
from a compound of the Formula X-1, wherein L¹ is a leaving
group;

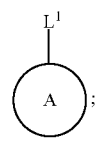

X-1 which comprises:
(g-2) reacting the compound of the Formula X-1 with a compound of Formula VII

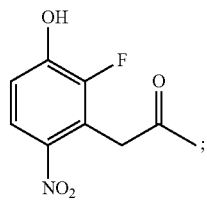

VII to form the compound of the Formula XIV-1:

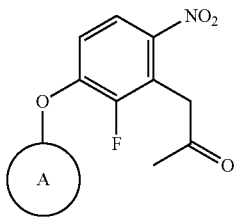

XIV-1

(i-2) reducing a compound of Formula XIV-1 to form a compound of Formula XI-1

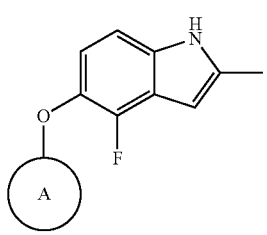

XI-1

Suitable rings systems for ring A are rings capable of being activated to allow displacement of the activating group by a phenolate ion, i.e. the structure of Formula VII. Such ring systems include:

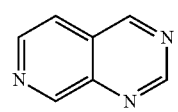

(i)

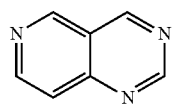

(ii)

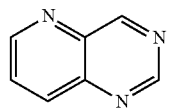

(iii)

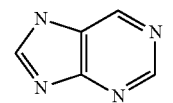

(iv)

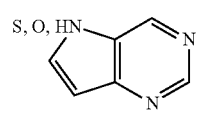

(v)

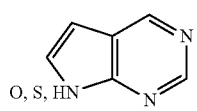

(vi)

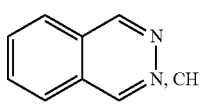

(vii)

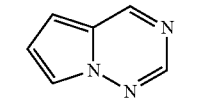

(viii)

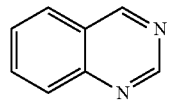

(ix)

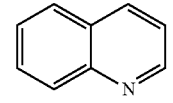

(x)

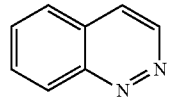

(xi)

In one embodiment ring A is selected from quinazoline, quinoline, cinnoline and pyrrolotriazine. In another embodiment ring A is quinazoline. In another embodiment ring A is pyrrolotriazine. In another embodiment ring A is quinazoline and $L^1$ is at the 4-position of the quinazoline ring. In another embodiment ring A is pyrrolotriazine and $L^1$ is at the 4-position of the pyrrolotriazine ring.

Examples of $L^1$ include chlorine, bromine, iodine and optionally substituted alkylsulphonyloxy or arylsulphonyloxy such as triflyloxy and p-tosyloxy.

Reaction Conditions for Process (g-2)

Reactions conditions for Process (g-2) are analogous to process conditions for process (g-1).

Reaction Conditions for Process (i-2)

Reactions conditions for Process (i-2) are analogous to process conditions for process (i-1).

The skilled person would understand that ring system A could be substituted by one or more groups. Such groups may be unaffected by the processes in this embodiment of the invention or may require protecting during the processes of this embodiment. The skilled man would be familiar with strategies to protect such group such as the use of protecting groups, the use of gentler reaction conditions which still facilitate the processes of the embodiment and/or the use of alternative catalysts. Conventional protecting groups may be used in accordance with standard practice (for illustration see T. W. Green, Protective Groups in Organic Synthesis, John Wiley and Sons, 1991) as described above.

In one aspect of the invention, following step (i-2) of the process, the compound of the Formula XI-1 is isolated and/or purified. Any suitable steps or procedures for isolating and/or purifying the desired product that are described in the literature and/or that are known to the skilled person may be used. Particular steps that would be of use would provide high quality and high purity product.

In another embodiment of the invention, following the step (i-2), the compound of Formula XI-1 is used in situ in the next step in the process.

A further embodiment of the invention provides a process for the manufacture of a compound of Formula XI-1 from a compound of Formula X-1 comprising the process steps (g-2) and (i-2) above.

In a further embodiment of the invention there is provided a compound of Formula XIV-1.

Minor variants to the above process are also included within the ambit of the invention. An example is where a compound of Formula VI,

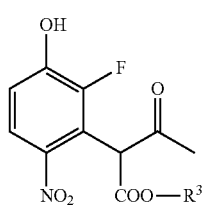

VI wherein $R^3$ is a suitable esterifying group as defined above, for example $C_{1-6}$alkyl or benzyl, is used in the place of a compound of Formula VII in process (g-2). Thus according to this further embodiment there is provided a process for the manufacture of a compound of Formula XI-1

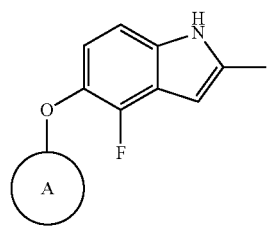

XI-1 from a compound of the Formula X-1, wherein $L^1$ is a leaving group;

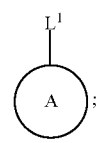

X-1 which comprises (g-3) reacting the compound of the Formula X-1 with a compound of Formula VI

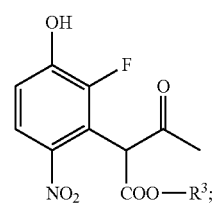

VI to form the compound of the Formula XIV-2:

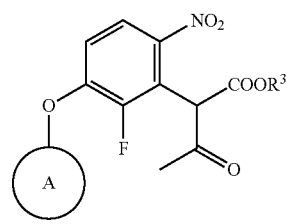

XIV-2

(i-2) reducing a compound of Formula XIV-2 to form a compound of Formula XI-2

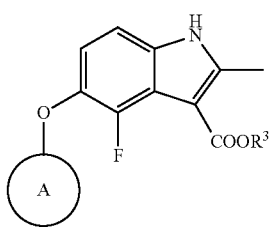

XI-2

(j-3) hydrolysing a compound of Formula XI-2 to form a compound of Formula XI-1.

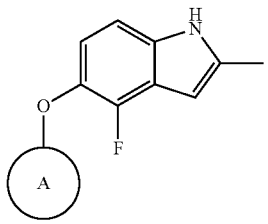

Examples of $L^1$ include chlorine, bromine, iodine and optionally substituted alkylsulphonyl such as triflyl and tosyl.

Reaction Conditions for Process (g-3)

Reactions conditions for Process (g-3) are analogous to process conditions for process (g-1).

Reaction Conditions for Process (i-3)

Reactions conditions for Process (i-3) are analogous to process conditions for process (i-1).

Reaction Conditions for Process (j-3)

The reaction of process (J-3) is conveniently carried out in a suitable solvent such as water or a water miscible solvent such as tetrahydrofuran or acetonitrile in the presence of a suitable base such as sodium hydroxide, potassium hydroxide or lithium hydroxide.

The reaction of step (J-3) is carried out at a temperature in the range, for example, of from 30 to 70° C., conveniently in the range of from 40 to 60° C., more conveniently in the range of from 45 to 55° C.

Examples of aryl-alkyl ammonium salts include Triton B (trimethyl benzyl ammonium hydroxide) which is commercially available. Examples of tetra-alkyl ammonium salts include tetra-butyl ammonium chloride and tetra-butyl ammonium bromide.

In one aspect of the invention, following step (j-3) of the process, the compound of the Formula XI-1 is isolated and/or purified. Any suitable steps or procedures for isolating and/or purifying the desired product that are described in the literature and/or that are known to the skilled person may be used. Particular steps that would be of use would provide high quality and high purity product.

In another embodiment of the invention, following the step (j-3), the compound of Formula XI-1 is used in situ in the next step in the process.

A further embodiment of the invention provides a process for the manufacture of a compound of Formula XI-1 from a compound of Formula X-1 comprising the process steps (g-3), (i-3) and (j-3) above.

In a further embodiment of the invention there are provided compounds of Formula XIV-2 and Formula XI-2.

According to a fourth aspect of the present invention, there is provided a process for the manufacture of 7-hydroxy-4-(4-fluoro-2-methylindol-5-yloxy)-6-methoxyquinazoline, a compound of the Formula XI:

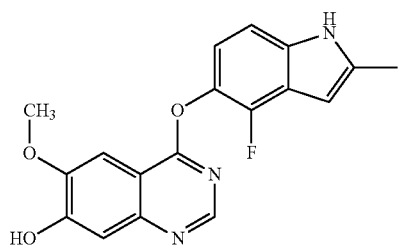

from a compound of the Formula IX:

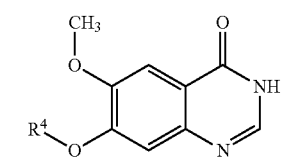

wherein $R^4$ is a protecting group which process comprises the steps of:

(f) reaction of a compound of Formula IX with a derivatizing agent to form a compound of Formula X wherein $L^1$ is a leaving group;

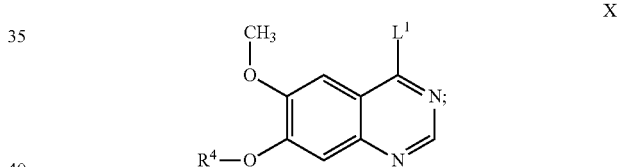

(g) reacting the compound of the Formula X with a compound of Formula II (2-methyl-4-fluoro-5-hydroxy-indole) in situ in the presence of the solvent used in step (f) to form the compound of the Formula VIII:

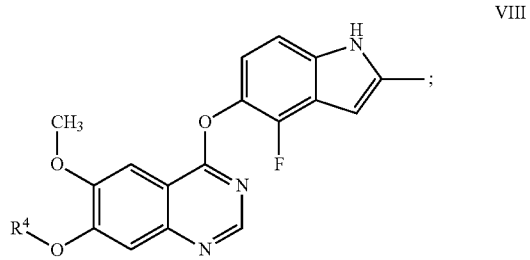

(h) isolating the compound of the Formula VIII; and (j) removing $R^4$ from the compound of the Formula VIII to form the compound of the Formula XI or a salt thereof (for example a potassium or sodium salt thereof);

and whereafter the compound of the Formula XI obtained in the form of the free acid may be converted into a salt form and the compound of the Formula XI obtained in the form of a salt may be converted into the free acid or into the form of an alternative salt, if necessary.

When the derivatizing agent is a chlorinating, brominating or iodinating agent the process step (f) could comprise:

(f) reacting the compound of the Formula IX with a suitable derivatizing agent in the presence of a suitable base and a solvent selected from toluene and anisole, wherein the reaction is carried out by:

(f-1) adding a mixture of the compound of the Formula IX and the base in the solvent to a mixture of the derivatizing agent in the solvent at a temperature in the range of from 60 to 110° C. over a period of about 60 minutes; or (f-2) adding the derivatizing agent to a mixture of the compound of the Formula IX and the base in the solvent at ambient temperature over a period of about 15 minutes and then heating the reaction mixture over a period of about 90 minutes to a temperature in the range of from 70 to 90° C. and stirring the reaction mixture at that is temperature for about 1 hour; or (f-3) adding the derivatizing agent to a mixture of the compound of the Formula IX and the base in the solvent at a temperature in the range of from 60 to 110° C. over a period of about 15 minutes, The process of the fourth aspect of the invention is advantageous in that it allows a compound of the Formula XI to be made in high purity and high yield on a larger scale.

In this aspect of the invention, following the manufacture of the compound of the Formula VIII in step (g), the compound is isolated and, optionally, purified in step (h) of the process. The isolated compound of the Formula VIII is then used in step (j) for manufacturing a compound of the Formula XI, either immediately or following storage for an appropriate period of time. The isolation of the compound of the Formula VIII in step (h) is advantageous because it enables a broader choice of methods for removing the $R^4$ group from the compound of the Formula VIII in step (j), for example compared to when this step is conducted in situ.

Reaction Conditions for Process (i)

The step (j) may comprise any suitable steps or procedures for removing $R^4$ that are described in the literature and/or that are known to the skilled person. Particular steps that would be of use would provide high quality and high purity product. For example, in step (j) when $R^4$ is a benzyl group this may be removed by catalytic hydrogenation, such as hydrogen gas and a suitable catalyst such as palladium on carbon. The use of catalytic hydrogenation is advantageous because it provides a highly efficient and mild method of removing the benzyl group and because it allows for the efficient removal of by-products from the waste stream.

The reaction of step (j) may be carried out at any temperature and in any solvent suitable for the particular method of removal of the benzyl group being used. For example with N-methylpyrrolidinone as solvent at a temperature between 20 to 60° C.

In one aspect of the invention, following step (j) of the process, the compound of the Formula XI is isolated and/or purified. Any suitable steps or procedures for isolating and/or purifying the desired product that are described in the literature and/or that are known to the skilled person may be used. Particular steps that would be of use would provide high quality and high purity product.

According to a fifth aspect of the invention, there is provided a process for the manufacture of AZD2171:

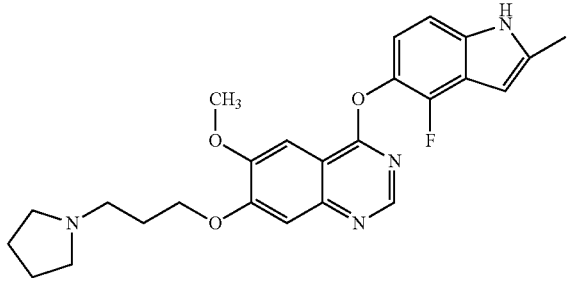

I (AZD2171)

from a compound of the Formula IX:

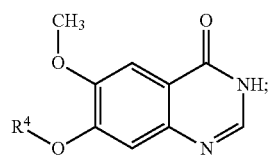

IX wherein $R^4$ is a protecting group.

which process comprises the steps of converting the compound of the Formula IX to a compound of the Formula XI:

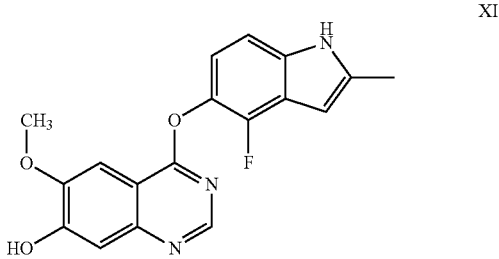 [SMILES: COc1cc2c(Oc3ccc4[nH]c(C)cc4c3F)ncnc2cc1O]

XI by conducting a process as discussed above in relation to the third or the fourth aspect of the invention; and (k) reacting the compound of the Formula XI with a compound of the Formula XII or a compound of Formula XIII

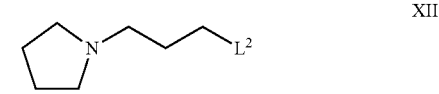

XII

XIII wherein $L^2$ is a leaving group and $X^-$ is a suitable counter ion such as $PF_6^-$ (hexafluorophosphate), chloride, bromide, or tetraphenylborate;

in the presence of a suitable base to provide a compound of the Formula I (AZD2171) or a salt thereof;

In one embodiment the compound of the Formula XII is provided as the hydrochloride salt. In another embodiment the compound of Formula XII is provided as the oxalate salt.

According to a further embodiment of the invention there is provided an oxalate salt of a compound of Formula XII.

Example of $L^2$ include chlorine, bromine, iodine, mesyloxy and tosyloxy. In another embodiment example of $L^2$ include chlorine, bromine and iodine.

In one embodiment in step (k) the compound of Formula XI is reacted with a compound of Formula XII. In another embodiment in step (k) the compound of Formula XI is reacted with a compound of Formula XIII.

And thereafter the compound of the Formula I obtained in the form of the free base may be converted into a salt form and the compound of the Formula I obtained in the form of a salt may be converted into the free base or into the form of an alternative salt, if necessary.

The process of the fifth aspect of the invention is advantageous in that it allows the compound of the Formula I to be made in high purity and high yield on a larger scale. Typically the process of the fifth aspect of the present invention proceeds in greater than 80% yield. The process of the fifth aspect of the invention is also advantageous for at least the reasons discussed above in relation to the third and fourth aspects of the invention.

In one embodiment the compound of the Formula XI is isolated and/or purified before step (k) is conducted, for example using any suitable steps or procedures that are described in the literature and/or that are known to the skilled person as discussed above. In another embodiment the compound of the Formula XI is reacted in-situ with a compound of Formula XII or Formula XIII.

Reaction Conditions for Process (k)

A suitable base for use in step (k) is selected from sodium carbonate, potassium carbonate, sodium hydroxide, potassium hydroxide, potassium tert-butoxide and cesium carbonate.

Step (k) may be conducted in any suitable solvent and at any suitable temperature.

When the base used in step (k) is selected from sodium carbonate and potassium carbonate, suitable solvents include, for example, N-methylpyrrolidinone and N,N-dimethylformamide. In this aspect, step (k) typically may be conducted at a temperature in the range of from 60 to 105° C., conveniently in the range of from 80 to 100° C., conveniently in the range of from 75 to 85° C.

The process of the fifth aspect of the invention is advantageous in that it allows the AZD2171 to be made in high purity and high yield on a larger scale. Typically, each of the steps of the process of the fifth aspect of the present invention proceeds in greater than 80% yield.

According to a sixth aspect of the present invention, there is provided a process for the manufacture of AZD2171 from a compound of the Formula IX:

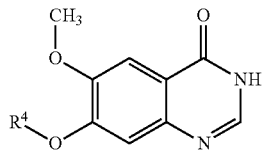

IX wherein $R^4$ is a protecting group.
which process comprises the steps of:
(f) reaction of a compound of Formula IX with a derivatizing agent to form a compound of Formula X wherein $L^1$ is a leaving group;

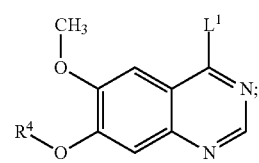

X (g) reacting the compound of the Formula X with 2-methyl-4-fluoro-5-hydroxy-indole, optionally in situ, optionally in the presence of the solvent used in step (f), to form a compound of the Formula VIII:

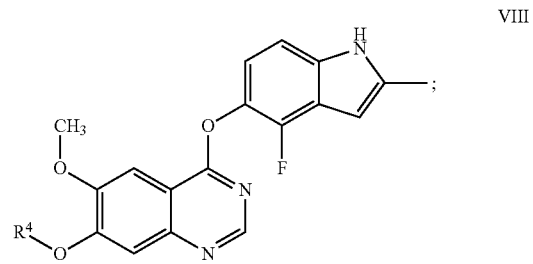

VIII (i) removing $R^4$ from the compound of the Formula VIII to form the compound of the Formula XI:

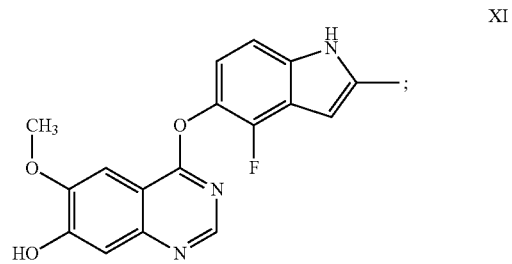 [SMILES: COc1cc2c(Oc3ccc4[nH]c(C)cc4c3F)ncnc2cc1O]

XI (k) reacting the compound of the Formula XI with a compound of the Formula XII or a compound of Formula XIII

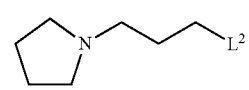

XII

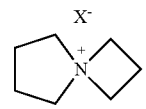

XIII wherein $L^2$ is a leaving group and $X^-$ is a suitable counter ion such as $PF_6^-$ (hexafluorophosphate), chloride or bromide; in the presence of a suitable base to provide a compound of the Formula I (AZD2171) or a salt thereof;
whereafter the AZD2171 obtained in the form of the free base may be converted into a pharmaceutically acceptable salt form, if necessary.

The process of the sixth aspect of the invention is advantageous in that it allows the AZD2171 to be made in high purity and high yield on a larger scale. Typically, each of the steps of the process of the seventh aspect of the present invention proceeds in greater than 80% yield.

When the derivatizing agent is a chlorinating, brominating or iodinating agent the process step (f) could comprise:

(f) reacting the compound of the Formula IX with a suitable derivatizing agent in the presence of a suitable base and a solvent selected from toluene and anisole, wherein the reaction is carried out by:
(f-1) adding a mixture of the compound of the Formula IX and the base in the solvent to a mixture of the derivatizing agent in the solvent at a temperature in the range of from 60 to 110° C. over a period of about 60 minutes; or
(f-2) adding the derivatizing agent to a mixture of the compound of the Formula IX and the base in the solvent at ambient temperature over a period of about 15 minutes and then heating the reaction mixture over a period of about 90 minutes to a temperature in the range of from 70 to 90° C. and stirring the reaction mixture at that temperature for about 1 hour; or
(f-3) adding the derivatizing agent to a mixture of the compound of the Formula IX and the base in the solvent at a temperature in the range of from 60 to 110° C. over a period of about 15 minutes, Preferred aspects of the process of the sixth aspect of the invention are as set out above in relation to individual steps as described in the second, third, fourth and fifth aspects of the present invention. In particular, preferred aspects of the process of the sixth aspect of the invention are as set out above, for example, in relation to individual steps of the third and fifth.

Conveniently, the base used in step (k) of the process of the sixth aspect of the present invention is potassium carbonate and the suitable solvent is N-methylpyrrolidinone.

The invention is illustrated hereinafter by means of the following non-limiting examples in which, unless otherwise stated:—

(i) evaporations were carried out by rotary evaporation in vacuo and work-up procedures were carried out after removal of residual solids such as drying agents by filtration;

(ii) yields are given for illustration only and are not necessarily the maximum attainable;

(iii) the structures of the end-products were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet; all samples run on a Bruker DPX 400 MHz at 300K in the solvent indicated, 16 scans, pulse repetition time 10 seconds;

(iv) intermediates were not generally fully characterised and purity was assessed by NMR analysis;

(v) chemical symbols have their usual meanings; SI units and symbols are used; and (vi) the following abbreviations have been used:

| | |
|---|---|
| THF | tetrahydrofuran |
| DMSO | dimethylsulfoxide |
| TFA | trifluoroacetic acid |
| NMP | N-methylpyrrolidinone |
| DMF | N,N-dimethylformamide |
| v/v | volume/volume ratio |
| w/w | weight/weight ratio |
| w/v | weight/volume ratio |

Example 1

Preparation of 4-fluoro-2-methyl-1H-indol-5-ol (Small Scale)

Preparation of tert-butyl 2-(2,3-difluoro-6-nitrophenyl)-3-oxobutanoate (Small Scale)

tert-Butyl acetoacetate (3.852 g) was added to a stirred mixture of sodium tert-pentoxide (2.804 g) in toluene (26 ml) at 40° C. The mixture was heated to 70° C. and 1,2,3-trifluoro-4-nitrobenzene (2.00 g) added. The mixture was maintained at 70° C. for 3 hours. The mixture was cooled to 25° C. and 20% w/w sulphuric acid added to adjust the mixture to pH 1. Sodium bicarbonate was added to bring the mixture to pH 5. Water (5 ml) and saturated sodium chloride (5 ml) was added. The lower aqueous layer was discarded and the organic layer is washed successively with water (7 ml), water (7 ml), 2.3% w/w aqueous sodium bicarbonate solution (2.75 ml) and then water (6 ml). The organic layer was distilled under reduced pressure (50 mbar), to leave a solution of tert-butyl 2-(2,3-difluoro-6-nitrophenyl)-3-oxobutanoate in toluene.

A small amount was vacuum distilled at 100° C., 0.4 mbar to give a purified sample of tert-butyl 2-(2,3-difluoro-6-nitrophenyl)-3-oxobutanoate Mass Spectrum [M–H]⁻ 314

1H NMR Spectrum (400 MHz, DMSO-$d_6$) δ ppm 1.27 (s, 9H keto) 1.30 (s, 9H enol) 1.86 (s, 3H enol) 2.45 (s, 3H keto) 5.66 (s, 1H keto) 7.60 (td, J=9.38, 7.97 Hz, 1H keto) 7.75 (td, J=9.35, 8.03 Hz, 1H enol) 7.91 (dt, J=9.19, 2.36 Hz, 1H keto) 8.05 (ddd, J=9.24, 4.71, 1.89 Hz, 1H enol) 13.12 (d, J=0.65 Hz, 1H enol)

Preparation of tert-butyl 2-(2-fluoro-3-hydroxy-6-nitrophenyl)-3-oxobutanoate (Small Scale)

The solution of tert-butyl 2-(2,3-difluoro-6-nitrophenyl)-3-oxobutanoate (3 g containing 2.38 g tert-butyl 2-(2,3-difluoro-6-nitrophenyl)-3-oxobutanoate) was diluted with toluene (5 ml) and extracted with a 40% w/w aqueous solution of Triton B (3.28 ml). To the aqueous extract was then added further 40% w/w aqueous Triton B (5.96 ml) and sodium hydroxide (2.053 g). The solution was heated at 50° C. for 18 hours. The solution was cooled to 25° C. and water (8.45 ml) added followed by 20% w/w sulphuric acid (14.3 ml) and then dichloromethane (4 ml). The organic layer was separated and the aqueous layer further extracted with dichloromethane (4 ml). The combined organic layers were distilled under reduced pressure to give tert-butyl 2-(2-fluoro-3-hydroxy-6-nitrophenyl)-3-oxobutanoate 1.59 g.

Mass Spectrum [M–H]⁻ 312

1H NMR Spectrum (400 MHz, DMSO-$d_6$) δ ppm 1.29 (s, 9H enol) 1.38 (s, 9H keto) 1.79 (s, 3H enol) 2.35 (s, 3H keto) 5.40 (s, 1H keto) 6.90 (t, J=9.05 Hz, 1H keto) 6.97 (t, J=9.00 Hz, 1H enol) 7.77 (d, J=9.05 Hz, 1H keto) 7.89 (dd, J=9.16, 1.40 Hz, 1H enol) 13.04 (br. s., 1H enol)

Preparation of 1-(2-fluoro-3-hydroxy-6-nitrophenyl)-propan-2-one (Small Scale)

To a solution of tert-butyl 2-(2-fluoro-3-hydroxy-6-nitrophenyl)-3-oxobutanoate (7.89 g) in dichloromethane was added trifluoroacetic acid (11.2 g) and the mixture stirred at ambient temperature for 20 hours. The mixture was concentrated to a thick paste and toluene (14 ml) added and the mixture distilled on a rotary evaporator (77 mbar, bath 40°

C.). Further toluene (14 ml) was added and the mixture distilled. Sodium hydroxide (7.4% w/w, 20 ml) was added and the lower aqueous layer separated and washed with toluene (18 ml). The aqueous layer was diluted with water (20 ml) and warmed to 40° C. Acetic acid (13 ml) was added followed by sulphuric acid (20% w/w, 20 ml). The mixture was cooled to 0° C. and further water (43 ml) added. The mixture was cooled to −5° C. and left overnight. The solid was filtered and washed with water (24 ml). The solid was dried in a vacuum oven to give 1-(2-fluoro-3-hydroxy-6-nitrophenyl)-propan-2-one (1.65 g, 30.7%).

Mass Spectrum [M−H]− 214
1H NMR Spectrum (400 MHz, DMSO-$d_6$) δ ppm 2.27 (s, 3H) 4.18 (d, J=1.62 Hz, 2H) 7.06 (t, J=9.00 Hz, 1H) 7.92 (dd, J=9.16, 1.72 Hz, 1H) 11.43 (br. s., 1H)

Preparation of 4-fluoro-2-methyl-1H-indol-5-ol (Small Scale)

1-(2-fluoro-3-hydroxy-6-nitrophenyl)-propan-2-one (1 g) was dissolved in a solution of potassium carbonate (1.3 g) in water (13 ml). A solution of sodium dithionite (5.24 g) in water (12.3 ml) was added dropwise. The mixture was stirred for 1.5 hours, then left to stand overnight. The solid was filtered and washed with water (6 ml). The solid was dried at 35° C. in a vacuum oven to give crude 4-fluoro-2-methyl-1H-indol-5-ol (0.5 g, 64.5%).

The crude solid (250 mg) was dissolved in dichloromethane (6.75 ml) and filtered through a pad of silica (250 mg). The filter pad was washed with dichloromethane (3.4 ml). The combined filtrates were distilled, removing 6 ml of dsitillate. The concentrate was then added dropwise to isohexane (4.25 ml) and the mixture concentrated, removing 3 ml of distillate. The mixture was cooled in an ice-bath and the precipitate filtered and washed with isohexane (0.9 ml). The solid was dried in a vacuum oven at 35° C. to give 4-fluoro-2-methyl-1H-indol-5-ol (180 mg, 72%)

Mass Spectrum [M+H]− 166
1H NMR Spectrum (400 MHz, DMSO-$d_6$) δ ppm 2.33 (s, 3H) 6.02-6.05 (m, 1H) 6.64 (t, J=8.41 Hz, 1H) 6.87 (d, J=8.51 Hz, 1H) 8.68 (s, 1H) 10.81 (br. s., 1H)

Example 2

Preparation of 4-fluoro-2-methyl-1H-indol-5-ol (Large Scale)

Preparation of tert-butyl 2-(2,3-difluoro-6-nitrophenyl)-3-oxobutanoate (Large Scale)

To toluene (810 l) was charged sodium tert-pentoxide (91 kg, 2.3 eq). The mixture was heated to 40° C. and tert-butyl acetoacetate (124.3 kg, 2.2 eq) added. The mixture was heated to 70° C. and trifluoronitrobenzene (63.1 kg, 1.0 eq) added. The temperature was maintained at 70° C. for 3 hours. The mixture was cooled to 25° C. and 20% w/w sulphuric acid added to adjust the pH to 5. The lower aqueous layer was discarded and the organic layer washed twice with water (2×227 kg of water), with 2.3% w/w sodium bicarbonate (192 kg) and then water (192 kg). The organic layer was distilled under vacuum (50 mbar), removing 574 kg of distillate leaving a solution of tert-butyl 2-(2,3-difluoro-6-nitrophenyl)-3-oxobutanoate in toluene.

Preparation of tert-butyl 2-(2-fluoro-3-hydroxy-6-nitrophenyl)-3-oxobutanoate (Large Scale)

The solution of tert-butyl 2-(2,3-difluoro-6-nitrophenyl)-3-oxobutanoate from above was extracted with 40% w/w aqueous Triton B (164 kg, 1.10 eq). To the aqueous phase was added further 40% w/w Triton B (298 kg, 2.0 eq) followed by sodium hydroxide (97 kg, 6.8 eq). The solution was heated at 50° C. for 18 hours. The mixture was cooled to 25° C. and water (392 kg) added followed by 20% w/w sulphuric acid (664 kg) and then dichloromethane (187 l). Further 20% w/w sulphuric acid was added until the mixture was pH 5. The organic layer was separated and the aqueous layer further extracted with dichloromethane (187 l). The combined organic layers were distilled under reduced pressure (500 mbar), removing 160 kg of distillate to give tert-butyl 2-(2-fluoro-3-hydroxy-6-nitrophenyl)-3-oxobutanoate as a solution in dichloromethane.

Preparation of 1-(2-fluoro-3-hydroxy-6-nitrophenyl)-propan-2-one (Large Scale)

To tert-butyl 2-(2-fluoro-3-hydroxy-6-nitrophenyl)-3-oxobutanoate in dichloromethane from above was added further dichloromethane (123 l) followed by trifluoroacetic acid (158 kg) whilst maintaining the temperature at 25° C. The reaction was stirred for 20 hours. The mixture was distilled, removing 283 kg of distillate. Toluene (176 l) was added and the mixture distilled, removing 208 kg of distillate. Further toluene (176 l) was added and the mixture distilled, removing 133 kg of distillate. To the residue was added 7.4% w/w aqueous sodium hydroxide (~705 kg) until the mixture was pH 10.5. The aqueous layer was separated and washed with toluene (250 l). The aqueous layer was diluted with water (250 l), heated to 40° C. and acetic acid (191.4 kg) added, reducing the pH from 10.1 to 3.8. The pH was then adjusted to 1 with 20% w/w sulphuric acid (~315 kg). The mixture was cooled to 0° C. and seeded with 1-(2-fluoro-3-hydroxy-6-nitrophenyl)-propan-2-one. Further water (600 kg) was added and the solid isolated by filtration. The filter cake was washed with water (300 l). The product was dried under vacuum (50 mbar) at 40° C. Yield: 56.0 kg, 74% based on 1,2,3-trifluoro-4-nitrobenzene.

Preparation of 4-fluoro-2-methyl-1H-indol-5-ol (Large Scale)

To a solution of potassium carbonate (79 kg) in water (800 kg) was added 1-(2-fluoro-3-hydroxy-6-nitrophenyl)-propan-2-one (61 kg) and the mixture stirred to give a solution. To this solution at 25° C. was added a solution of sodium dithionite (298 kg) in water (750 kg). The mixture was held at 25° C. for 2 hours. The product was isolated by filtration, washing the filter cake with water (366 kg). The product was dried under reduced pressure (50 mbar) at 35° C. Yield: 34 kg, 72%.

The crude 4-fluoro-2-methyl-1H-indol-5-ol (33 kg) was dissolved in dichloromethane (880 l) and filtered through silica (33 kg). The filter was washed with dichloromethane (440 l). The combined filtrates were distilled, removing 835 l of distillate. This concentrate was added rapidly to isohexane (360 kg), resulting in a suspension. The batch was distilled, removing 436 l of distillate. The batch was cooled to 0° C., aged for 1 hour and then filtered. The filter cake was washed with isohexane (73 kg). The product was dried under pressure (50 mbar) at 35° C. Yield: 31 kg, 68% based on 1-(2-fluoro-3-hydroxy-6-nitrophenyl)-propan-2-one.

Example 3

Preparation of 1-(2-fluoro-3-hydroxy-6-nitrophenyl)-propan-2-one from methyl acetoacetate

Preparation of Methyl 2-(2,3-difluoro-6-nitrophenyl)-3-oxobutanoate

Sodium tert-pentoxide (13.41 g) was added to mesitylene (112 ml) and the slurry heated to 50° C. to give a red/brown solution. To this was added methyl acetoacetate (14.28 g). The mixture exothermed to 75° C., giving a thick orange/yellow slurry. The temperature was adjusted to 70° C. and 1,2,3-trifluoro-4-nitrobenzene (10.0 g) added, giving an orange solution. The mixture was maintained at about 70° C. for 3 hours, then allowed to cool to ambient and left overnight. To the mixture was added hydrochloric acid (6% w/w, 43 ml). The lower aqueous layer was separated and the organic layer further washed twice with hydrochloric acid (6% w/w, 36 ml). The organic layer was washed with aqueous sodium bicarbonate solution (2.3% w/w, 15 ml) and then water (30 ml). Further mesitylene (21 ml) was charged and the mixture evaporated on a rotary evaporator (25 mbar, bath 40° C.), giving 25 ml of solution.

A small amount of this solution (5 ml) was concentrated (68° C., 10 mbar) to give methyl 2-(2,3-difluoro-6-nitrophenyl)-3-oxobutanoate (2.22 g) as a yellow/brown oil.

Mass Spectrum [M−H]⁻ 272

1H NMR Spectrum (400 MHz, DMSO-$d_6$) δ ppm 1.85 (s, 3H enol) 2.47 (s, 3H keto) 3.50 (s, 3H keto*) 3.63 (s, 3H enol*) 5.79 (s, 1H keto) 7.63 (td, J=9.38, 7.97 Hz, 1H keto) 7.78 (d, J=9.38, 7.97 Hz, 1H enol) 7.93 (ddd, J=9.21, 4.69, 1.94 Hz, 1H keto) 8.08 (ddd, J=9.27, 4.74, 1.94 Hz, 1H enol) 12.88 (s, 1H enol)

*=interchangeable

Preparation of Methyl 2-(2-fluoro-3-hydroxy-6-nitrophenyl)-3-oxobutanoate

To a solution of methyl 2-(2,3-difluoro-6-nitrophenyl)-3-oxobutanoate in mesitylene (11.01 g, 20 ml of solution) was added Triton B (40% w/w, 50.54 g). The separation was poor so further mesitylene (8 ml) was added. The lower aqueous layer was separated and further Triton B (40% w/w, 50.54 g) added to it. The aqueous mixture was held at 55° C. for 16 hours. The mixture was cooled to ambient and hydrochloric acid (32% w/w, 19 ml) added over 15 minutes until the pH was 5. Dichloromethane (24 ml) was added and the lower organic layer separated. The aquous layer was further extracted with dichloromethane (24 ml) and the combined organic phase basified by the addition of aqueous sodium hydroxide (8.5% w/w, 23 ml) to pH 10.5. The aqueous phase was further washed with isohexane (23 ml), to give an aqueous solution of methyl 2-(2-fluoro-3-hydroxy-6-nitrophenyl)-3-oxobutanoate.

A small amount was evaporated to dryness on a rotary evaporator to give a sample for analysis.

Mass Spectrum [M−H]⁻ 270

1H NMR Spectrum (400 MHz, DMSO-$d_6$) δ ppm 1.75 (s, 3H enol) 3.59 (s, 3H enol) 6.56 (t, J=9.27 Hz, 1H enol) 7.86 (dd, J=9.43, 1.24 Hz, 1H enol) 12.72 (br. s., 1H enol)

Preparation of 1-(2-fluoro-3-hydroxy-6-nitrophenyl)-propan-2-one

Water (17.7 ml) was added to acetic acid (15.6 ml) followed by sulphuric acid (16.6 ml). To this solution was added an aqueous solution containing methyl 2-(2-fluoro-3-hydroxy-6-nitrophenyl)-3-oxobutanoate (8.195 g) and the mixture heated at 90° C. for 4 hours. The mixture was cooled to 80° C. and water (24.6 ml) added. The mature was cooled to 40° C. and a seed of 1-(2-fluoro-3-hydroxy-6-nitrophenyl)-propan-2-one (2 mg) added. The mixture was cooled to 0° C. and left to stir overnight. The solid was filtered, washed three times with water (15 ml) and dried under vacuum at 40° C. to give 1-(2-fluoro-3-hydroxy-6-nitrophenyl)-propan-2-one (320 mg,)

Mass Spectrum [M−H]⁻ 214

1H NMR Spectrum (400 MHz, DMSO-$d_6$) δ ppm 1.75 (s, 3H enol) 3.59 (s, 3H enol) 6.56 (t, J=9.27 Hz, 1H enol) 7.86 (dd, J=9.43, 1.24 Hz, 1H enol) 12.72 (br. s., 1H enol)

Example 4

Preparation of 1-(2-fluoro-3-hydroxy-6-nitrophenyl)-propan-2-one from ethyl acetoacetate

Preparation of Ethyl 2-(2,3-difluoro-6-nitrophenyl)-3-oxobutanoate

Sodium tert-pentoxide (33.52 g) was added to mesitylene (280 ml) and the mixture heated to 50° C. To the suspension was added ethyl acetoacetate (39.61 g) over 10 minutes. The reaction mixture exothermed to about 60° C. The thick slurry was heated to 70° C. and 1,2,3-trifluoro-4-nitrobenzene (25.0 g) added. The mixture exothermed to 80° C. The mixture was held at 70-80° C. for 3 hours, then allowed to cool to ambient and left overnight. To the mixture was added hydrochloric acid (6% w/w, 100 ml), until the pH reached 1. The aqueous layer was separated and discarded and the organic layer washed twice with hydrochloric acid 6% w/w, 90 ml), then with aqueous sodium bicarbonate (2.3% w/w, 37.5 ml) and finally water (75 ml). To the organic layer was added further mesitylene (53 ml) and the mixture distilled on a rotary evaporator (10 mbar, bath 60° C.) to give a solution of ethyl 2-(2,3-difluoro-6-nitrophenyl)-3-oxobutanoate in mesitylene (90 ml containing 36.22 g of ethyl 2-(2,3-difluoro-6-nitrophenyl)-3-oxobutanoate).

A small sample (10 ml) was further evaporated on a rotary evaporator (12 mbar, bath 60° C.)

Mass Spectrum [M−H]⁻ 284

1H NMR Spectrum (400 MHz, DMSO-$d_6$) δ ppm 1.03 (t, J=7.11 Hz, 3H keto*) 1.05 (t, J=7.11 Hz, 3H enol*) 1.86 (s, 3H enol) 2.47 (s, 3H keto) 3.89-4.22 (m, 2H keto+2H enol) 5.76 (s, 1H keto) 7.62 (td, J=9.32, 7.97 Hz, 1H keto) 7.78 (td, J=9.35, 8.03 Hz, 1H enol) 7.93 (ddd, J=9.19, 4.71, 1.94 Hz, 1H keto) 8.08 (ddd, J=9.27, 4.69, 1.99 Hz, 1H enol) 13.00 (s, 1H enol)

Preparation of Ethyl 2-(2-fluoro-3-hydroxy-6-nitrophenyl)-3-oxobutanoate

A solution of ethyl 2-(2,3-difluoro-6-nitrophenyl)-3-oxobutanoate (34.56 g) in mesitylene (total volume 80 ml) was extracted with Triton B (40% w/w, 140.4 g). The aqueous layer was further diluted with Triton B (40% w/w, 140.4 g), heated to 50° C. and held for 16 hours. The mixture was cooled to ambient and acified to pH 5 by the addition of hydrochloric acid (32% w/w, 74 ml). The mixture is extracted twice with dichloromethane (69 ml) and the combined organic layers extracted with aqueous sodium hydroxide (8.5% w/w, 67 ml). The aqueous extract was washed twice with isohexane (67.5 ml) to give an aqueous solution of ethyl 2-(2-fluoro-3-hydroxy-6-nitrophenyl)-3-oxobutanoate (80 ml, containing 31.92 g of ethyl 2-(2-fluoro-3-hydroxy-6-nitrophenyl)-3-oxobutanoate assuming 100% yield). A small sample was evaporated to dryness on a rotary evaporator and analysed.

Mass Spectrum [M–H]⁻ 286
1H NMR Spectrum (400 MHz, DMSO-$d_6$) δ ppm 0.91 (t, J=7.06 Hz, 3H) 1.49 (s, 3H) 3.58-3.89 (m, 2H) 5.97 (t, J=9.32 Hz, 1H) 7.68 (d, J=10.34 Hz, 1H)

Preparation of 1-(2-fluoro-3-hydroxy-6-nitrophenyl)-propan-2-one

To a mixture of acetic acid (57 ml) and water (68 ml) was added sulphuric acid (61 ml). The mixture was warmed to 97° C. and an aqueous solution containing ethyl 2-(2-fluoro-3-hydroxy-6-nitrophenyl)-3-oxobutanoate (31.6 g) added. The mixture was heated at 97° C. for 3.5 hours, then cooled to 80° C. and water (95 ml) added. The mixture was cooled to 40° C. and seeded with 1-(2-fluoro-3-hydroxy-6-nitrophenyl)-propan-2-one (2 mg). The mixture was cooled to 0° C. and stirred overnight. The mixture was filtered and washed three times with water (58 ml). The product was dried in a vacuum oven to give 1-(2-fluoro-3-hydroxy-6-nitrophenyl)-propan-2-one (8.42 g, 35.7%).

Mass Spectrum [M–H]⁻ 212
1H NMR Spectrum (400 MHz, DMSO-$d_6$) δ ppm 2.27 (s, 3H) 4.18 (s, 2H) 7.06 (t, J=8.94 Hz, 1H) 7.92 (dd, J=9.21, 1.67 Hz, 1H) 11.44 (br. s., 1H)

Example 5

Preparation of 7-(Benzyloxy)-4-[(4-fluoro-2-methyl-1H-indol-5-yl)oxy]-6-methoxyquinazoline 7-benzyloxy-6-methoxy-3,4-dihydroquinazolin-4-one (28 kg) and triethylamine hydrochloride (2.7 kg) were added to anisole (244 kg). N,N-Diisopropylethylamine (19.2 kg) was added, followed by a line wash of anisole (20 kg). The mixture was cooled to 15° C. and phosphorus oxychloride (19.8 kg) added over 5 minutes, followed by a line wash of anisole (13.9 kg). After stirring for 15 minutes the mixture was heated to 80° C. over 90 minutes and held at 80° C. for 1 hour. When the reaction was complete the batch was transferred to a new reactor, followed by a line wash of anisole (39.7 kg). The mixture was cooled to 40° C. and 16.19% w/w aqueous sodium hydroxide solution (132 kg) added over 15 minutes, allowing the temperature to rise to 50° C., followed by a line wash of water (5 kg). The mixture was held at 50° C. for 30 minutes, then heated to 80° C. The batch was filtered through a Gaf filter, followed by a line-wash of anisole (10 kg). The lower aqueous layer was separated and the upper organic layer washed at 80° C. with 20.9% w/w aqueous sodium chloride solution (98.2 kg). The mixture was distilled under reduced pressure (80 mbar) to leave a residual volume of 224 l. 1-Methyl-2-pyrrolidinone (28.9) was added and the mixture heated to 80° C. to give a solution of 7-(benzyloxy)-4-chloro-6-methoxyquinazoline.

4-Fluoro-2-methyl-1H-indol-5-ol (17.2 kg) was dissolved in acetonitrile (85 kg). The solution was degassed by holding under vacuum (150 mbar) and then pressurising to 21.6 bar with nitrogen. This was carried out four times. The solution was cooled to 0° C. and a 16.19% w/w aqueous sodium hydroxide solution (25.7 kg) added over 15 minutes, maintaining the temperature at 0° C., followed by a line wash of acetonitrile (3 kg). This cold solution was is added over 45 minutes to the solution of 7-(benzyloxy)-4-chloro-6-methoxyquinazoline at 80° C., followed by a line wash of acetonitrile (22 kg). The mixture was held at 80° C. for 4 hours, then washed twice with water (42 kg). The mixture was cooled to 20° C. and distilled under reduced pressure (250 mbar) until the batch temperature reached 70° C. The vacuum was then adjusted to 80 mbar and the distillation continued to a residual volume of 168 l. The batch was cooled to 65° C. and a solution of water (56 kg) in methanol (133 kg) added, maintaining the temperature at 60-65° C. The mixture was cooled to 20° C. over 1 hour, then held at 20° C. for 2 hours. The product was isolated by filtration, washing the cake twice with methanol (33 kg). The product was dried with nitrogen at 40° C. Yield: 32.7 kg, 77%.

Mass Spectrum [M+H]⁻ 430
1H NMR Spectrum (400 MHz, DMSO-$d_6$) δ ppm 2.42 (s, 3H) 4.00 (s, 3H) 5.36 (s, 2H) 6.24 (s, 1H) 6.99 (dd, J=8.57, 7.49 Hz, 1H) 7.16 (d, J=9.05 Hz, 1H) 7.35-7.41 (m, 1H) 7.41-7.47 (m, 2H) 7.51 (s, 1H) 7.50-7.55 (m, 2H) 7.63 (s, 1H) 8.50 (s, 1H) 11.33 (br. s., 1H)

The 7-benzyloxy-6-methoxy-3,4-dihydroquinazolin-4-one starting material was prepared as follows:

A mixture of vanillic acid (200 g), acetonitrile (600 ml) and N-ethyldiisopropylamine (580 ml) was heated to reflux. Benzyl bromide (347 ml) was then added over a period of 3 hours. The reaction mixture was held at reflux for 15 hours. Triethylamine (50 ml) was added and the reaction mixture held at reflux for a further 30 minutes. Acetonitrile (400 ml) was added and the reaction mixture heated to 81° C. Water (300 ml) was added and the reaction mixture cooled to 45° C. The reaction mixture was held at 45° C. for 30 minutes until crystallisation occurred. The reaction mixture was then allowed to cool to 24° C. and then further cooled to 8° C. and the product (benzyl 4-(benzyloxy)-3-methoxybenzoate) isolated by filtration. The solid was washed with water (3×500 ml) and then dried under vacuum at 45° C. Yield: 387 g, 93.4%

Mass Spectrum (M+H)⁻=349.2
1H NMR Spectrum (CDCl₃) 3.9 (s, 3H), 5.2 (s, 2H), 5.3 (s, 2H), 6.9 (d, 1H), 7.2-7.4 (m, 10H), 7.6-7.7 (m, 2H)

Benzyl 4-(benzyloxy)-3-methoxybenzoate (78 g) was mixed with dichloromethane (580 ml), water (72 ml) and glacial acetic acid (288 ml). The mixture was cooled to 10° C. Concentrated sulfuric acid (108 ml) was added in a controlled manner maintaining the temperature of the reaction mixture below 25° C. Concentrated nitric acid (17.5 ml) was then added keeping the temperature of the reaction mixture below 20° C. The reaction mixture was then stirred at 20° C. for 23 hours. The lower aqueous layer was removed and the organic layer was washed with water (290 ml). The organic layer was separated and distilled to 270 ml at atmospheric pressure. Isopropanol (750 ml) was added to the reaction mixture at 45° C. The reaction mixture was then heated to 40° C. and stirred at this temperature for 15 minutes. The resulting suspension was then cooled to 20° C., then to 5° C. and held at this temperature for one hour. The product (benzyl 4-(benzyloxy)-5-methoxy-2-nitrobenzoate) was isolated by filtration, washed with isopropanol (200 ml) and dried at less than 25° C. Yield: 78.4 g, 89.6%;

Mass Spectrum (M+H)⁻=394.1.
1H NMR Spectrum (CDCl₃) 3.9 (s, 3H), 5.2 (s, 2H), 5.3 (s, 2H), 7.1 (s, 1H), 7.3-7.4 (m, 10H), 7.5 (s, 1H);

Benzyl 4-(benzyloxy)-5-methoxy-2-nitrobenzoate (77 g) was dissolved in acetonitrile (882 ml). Sodium dithionite (160.5 g) was added to the solution and the temperature adjusted to 25° C. Water (588 ml) was then added, maintaining the temperature at 25° C. The pH was maintained at 6 using 8.8 M sodium hydroxide during the reduction. The slurry was then heated to 65° C. and the lower aqueous phase was removed. Concentrated hydrochloric acid (35% w/w, 7.25 ml) was then added. The slurry was allowed to cool to 40° C. and then to 20° C. Sodium hydroxide solution (47% w/w, 12.4 ml) was added and the slurry cooled to 0° C. The product (benzyl 2-amino-4-(benzyloxy)-5-methoxybenzoate) was isolated by filtration, washed with water (2×196 ml) and then dried at 40° C. under vacuum. Yield: 66.2 g, 92.4%;

Mass Spectrum (M+H)⁻=364.1.
$^1$H NMR Spectrum (CDCl$_3$) 3.8 (s, 3H), 5.1 (s, 2H), 5.3 (s, 2H), 6.2 (s, 1H), 7.3-7.4 (m, 10H);

Benzyl 2-amino-4-(benzyloxy)-5-methoxybenzoate (5.55 kg), formamidine acetate (2.2 kg) and isobutanol (33.3 L) were mixed. The reaction mixture was then heated to 97° C. and stirred at this temperature for 6 hours. The reaction mixture was then cooled to 25° C. over a period of at least an hour and then stirred at this temperature for 30 minutes. The product (7-benzyloxy-6-methoxy-3,4-dihydroquinazolin-4-one) was isolated by filtration, washed with isobutanol (6.1 L) and dried in the vacuum oven at a temperature of from 40 to 45° C.

Yield: 4.25 kg, 98%
Mass Spectrum (M+H)⁻=283.1.
$^1$H NMR Spectrum (DMSOd$_6$) 3.9 (s, 3H), 5.3 (s, 2H), 7.3 (s, 1H), 7.3-7.5 (m, 6H), 8.0 (s, 1H);

Example 6

Preparation of 4-[(4-fluoro-2-methyl-1H-indol-5-yl)oxy]-6-methoxy-7-[3-(pyrrolidin-1-yl)propoxy]quinazoline 7-(Benzyloxy)-4-[(4-fluoro-2-methyl-1H-indol-5-yl)oxy]-6-methoxyquinazoline (40 kg) was dissolved in 1-methyl-2-pyrrolidinone (206 kg) at 40-45° C. This solution was charged to an inerted pressure vessel containing 10% palladium on carbon catalyst (0.235 kg of approximately 50% water wet catalyst). A line wash of 1-methyl-2-pyrrolidinone at 40-45° C. (35 kg) was applied. The mixture was hydrogenated at 45° C. and 3 barg for 3.5 hours. The reactor was purged with nitrogen and recirculated through a Gaf filter before being filtered through a 1 μm Pall filter into a new reactor. A line wash of 1-methyl-2-pyrrolidinone (66 kg) through the filters was applied to give a solution of 4-[(4-fluoro-2-methyl-1H-indol-5-yl)oxy]-6-methoxyquinazolin-7-ol. To this solution was added potassium carbonate (10.3 kg) and the mixture heated to 80° C.

A 71.5% w/w aqueous solution of 1-(3-chloropropyl)pyrrolidine hydrochloride (25 kg) was diluted with water (14 l) and methyl tert-butyl ether (12 l) added. The stirred mixture was basified to pH>11 by addition of 46% w/w aqueous sodium hydroxide solution (6.5 l). The layers were separated and he lower aqueous phase was further extracted with methyl tert-butyl ether (12 l). The combined organic layers were washed with 20% w/w aqueous sodium chloride solution (12.5 kg) to give a solution of 1-(3-chloropropyl)pyrrolidine in methyl tert-butyl ether.

The solution of 1-(3-chloropropyl)pyrrolidine in methyl tert-butyl ether was added to the hot solution of 4-[(4-fluoro-2-methyl-1H-indol-5-yl)oxy]-6-methoxyquinazolin-7-ol in 1-methyl-2-pyrrolidinone. A line wash of methyl tert-butyl ether (4 kg) was applied. The mixture was maintained at 80° C. for 3 hours, then water (348 kg) was added over 2 hours. The suspension was cooled to 60° C. over 4 hours and held at 60° C. for 12 hours. The product was isolated by filtration and the cake washed with 1:1 w/w 1-methyl-2-pyrrolidinone/water (64 kg), then three times with water (62 kg). The product was dried with hot nitrogen at 45° C.

Yield: 34.8 kg at 100% w/w, 83%.
Mass Spectrum [M+H]⁻ 451
1H NMR Spectrum (400 MHz, DMSO-d$_6$) δ ppm 1.66-1.73 (m, 4H) 1.95-2.03 (m, 2H) 2.42 (s, 3H) 2.43-2.48 (m, 4H) 2.57 (t, J=7.11 Hz, 2H) 4.00 (s, 3H) 4.25 (t, J=6.41 Hz, 2H) 6.24 (s, 1H) 6.99 (dd, J=8.51, 7.44 Hz, 1H) 7.16 (d, J=8.62 Hz, 1H) 7.38 (s, 1H) 7.60 (s, 1H) 8.50 (s, 1H) 11.33 (br. s., 1H)

The aqueous 1-(3-chloropropyl)pyrrolidine hydrochloride solution was prepared as follows:

A solution of 1-bromo-3-chloropropane (99.5 kg) in toluene (237 kg) was heated to 40-45° C. To this solution was added pyrrolidine (94.5 kg) over 1.5 hours, maintaining the temperature at 40-45° C. A line wash of toluene (37 kg) was applied and the reaction maintained at 40-45° C. for a further four hours. The reaction mixture was cooled to 20-25° C. and washed with water (211 kg). Further water (138 kg) was added and the pH adjusted to 8.8-9.0 by the addition of 34% w/w hydrochloric acid (4.7 kg). The aqueous phase was separated and discarded. To the organic phase was added 34% w/w hydrochloric acid (61 kg) until the pH was 0.5-1.0. The aqueous was separated and concentrated under vacuum, maintaining the temperature <50° C. until the toluene content was <0.1%, giving an aqueous solution of 1-(3-chloropropyl)pyrrolidine hydrochloride 129.1 kg at 71.5% w/w, 79.9%

Mass Spectrum [M+H]⁻ 148
1H NMR Spectrum (400 MHz, DMSO-d$_6$) δ ppm 1.79-2.06 (m, 4H) 2.12-2.24 (m, 2H) 2.90-3.03 (m, 2H) 3.15-3.24 (m, 2H) 3.44-3.56 (m, 2H) 3.76 (t, J=6.41 Hz, 2H) 11.33 (br. s., 1H)

4-[(4-fluoro-2-methyl-1H-indol-5-yl)oxy]-6-methoxy-7-[3-(pyrrolidin-1-yl)propoxy]quinazoline can be similarly prepared by using a methyl tert-butyl ether solution of 1-(3-chloropropyl)pyrrolidine prepared from 1-(3-chloropropyl)pyrrolidine oxalate.

1-(3-Chloropropyl)pyrrolidine oxalate (134.8 kg) was suspended in water (226 l) and methyl tert-butyl ether (83.4 kg) added. The stirred mixture was basified to pH>11 by addition of 49% w/w aqueous potassium hydroxide solution (138.9 kg). A line wash of water (22.6 l) was applied. The lower aqueous layer was separated and transferred to a second reactor. The upper organic layer was transferred to 200 l drums. A line wash of methyl tert-butyl ether (16.7 kg) was applied. The aqueous layer was recharged to the original reactor and further extracted with methyl tert-butyl ether (83.4 kg). The lower aqueous layer was discarded. The original organic layer was recharged from the drums. A line wash of methyl tert-butyl ether (16.7 kg) was applied. The combined organic layers were washed with 23% w/w aqueous potassium chloride solution (64.8 kg) to give a solution of 1-(3-chloropropyl)pyrrolidine (83.9 kg) in methyl tert-butyl ether. The required amount of solution can then be used as appropriate.

1-(3-Chloropropyl)pyrrolidine oxalate was prepared as follows:

To a solution of 1-bromo-3-chloropropane (190 g) in toluene (455 ml) at 40° C. was added pyrrolidine (173 g), maintaining the temperature at 40-45° C. A line wash of toluene (40 ml) was then applied. The mixture was maintained at 40-45° C. for 4 hours, then cooled to 20° C. and held for 6 hours. The mixture was washed with water (400 ml), and then further water (265 ml) added and the pH adjusted to 8.8-9.0 with extracted with 37% hydrochloric acid (9.5 ml). The aqueous layer was separated.

The organic layer was added to a solution of oxalic acid dihydrate (129.31 g) in a mixture of isopropanol (1070 ml)

and water 109 ml) over 1 hour at 65-70° C. The mixture was cooled to 55° C. and held at this temperature for 30 minutes to initiate crystallisation. The mixture was then cooled to 10° C. over 1.5 hours, and held at 10° C. for an hour before filtering. The solid was washed with methyl tert-butyl ether (400 ml) and finally methyl tert-butyl ether (300 ml). The solid was dried at 40° C. in a vacuum oven to give 1-(3-chloropropyl)pyrrolidine oxalate.

Yield 208.23 g, 72.5% of theoretical Mass Spectrum [M+H]$^-$ 148

1H NMR Spectrum (400 MHz, DMSO-d$_6$) δ ppm 1.85-1.97 (m, 4H) 2.06-2.16 (m, 2H) 3.12-3.30 (m, 6H) 3.71 (t, J=6.41 Hz, 2H) 9.47 (br. s., 1H)

Example 7

Preparation of 4-[(4-fluoro-2-methyl-1H-indol-5-yl)oxy]-6-methoxy-7-(3-pyrrolidin-1-ylpropoxy)quinazoline maleate salt 4-[(4-fluoro-2-methyl-1H-indol-5-yl)oxy]-6-methoxy-7-(3-pyrrolidin-1-ylpropoxy)quinazoline (28.4 kg at 100% w/w) was suspended in methanol (284 l). The mixture was degassed by holding under vacuum (−0.7 barg), then releasing the vacuum with nitrogen. This was carried out three times. The slurry was heated to reflux to give a clear solution. The solution was cooled to 60° C. and recirculated through a Gaf filter, before being filtered through a 1 μm Pall filter into the crystalliser. A line wash of methanol (85 l) was applied, after being degassed as before.

Methanol (114 l) was cooled to 0° C. and degassed as above. Maleic acid (6.96 kg) was added and the mixture stirred to give a clear solution whilst maintaining the temperature at 0° C. This was transferred via a 1 μm Pall filter to the crystalliser, maintaining the temperature in the crystalliser at 55-60° C. A line wash of methanol (43 l) was applied. The temperature was adjusted to 55° C. and micronised 4-[(4-fluoro-2-methyl-1H-indol-5-yl)oxy]-6-methoxy-7-(3-pyrrolidin-1-ylpropoxy)quinazoline maleate salt (Form A, 0.43 kg) was added. The mixture was held at 55° C. for 3 hours, then cooled to 40° C. over 7 hours, then cooled to −5° C. over 6 hours. The suspension was held at −5° C. for 20 hours. The product was isolated by filtration, washing the cake with methanol (128 l). The product was dried under hot nitrogen at 50° C. Yield: 27.3 kg, 76%

Mass Spectrum [M+H] 451

1H NMR Spectrum (400 MHz, DMSO-d$_6$) δ ppm 1.97 (br. s., 4H) 2.17-2.29 (m, 2H) 2.42 (s, 3H) 3.13 (br. s., 2H) 3.32-3.38 (m, 2H) 3.60 (br. s., 2H) 4.01 (s, 3H) 4.32 (t, J=6.03 Hz, 2H) 6.01 (s, 2H) 6.24 (s, 1H) 6.98 (dd, J=8.51, 7.44 Hz, 1H) 7.16 (d, J=8.73 Hz, 1H) 7.43 (s, 1H) 7.64 (s, 1H) 8.52 (s, 1H) 9.36 (br. s., 2H) 11.33 (br. s., 1H)

Example 8

Preparation of 4-[(4-fluoro-2-methyl-1H-indol-5-yl)oxy]-6-methoxy-7-(3-pyrrolidin-1-ylpropoxy)quinazoline using 4-azoniaspiro[3,4]octane salts Preparation of 4-azoniaspiro[3,4]octane chloride 1-(3-Chloropropyl)pyrrolidine (1.142 g) was dissolved in methanol (38 ml) and the solution refluxed overnight. The solution was evaporated to dryness on a rotary evaporator to give 4-azoniaspiro[3,4]octane chloride as an impure oil.

Yield 1.14 g

1H NMR Spectrum (400 MHz, DMSO-d$_6$) δ ppm 1.90-2.00 (m, 4H) 2.4-2.48 (m, 2H) 3.54-3.61 (m, 4H) 4.27 (t, J=8.1 Hz, 4H)

M$^+$ 112

Preparation of 4-azoniaspiro[3,4]octane hexafluorophosphate

An aqueous solution of 4-azoniaspiro[3,4]octane chloride was prepared by adding 1-(3-Chloropropyl)pyrrolidine (128 ml) to water (100 ml) at 94° C. over 25 minutes. The mixture was stirred for a further 5 minutes to give a clear yellow solution. This was cooled to 20° C. and stored in a bottle. Line washes of water (2×25 ml) were applied.

4-Azoniaspiro[3,4]octane chloride solution in water (88 ml) was added over 10 minutes to a solution of sodium hexaflurophosphate (50.3 g) in water (100 ml), followed by a line wash of water (12 ml). Further water (50 ml) was added to aid stirring of the thick suspension. The mixture was heated to 90° C. to aid stirring. The solid was filtered and washed with water (2×100 ml) and dried in a vacuum oven to give 4-azoniaspiro[3,4]octane hexafluorophosphate (54.14 g, 70.3% of theory).

Infra Red (KBr Disc) wavenumber (cm$^{-1}$) 1450, 1348, 1323, 1100, 831, 557

1H NMR Spectrum (400 MHz, DMSO-d$_6$) δ ppm 1.89-2.01 (m, 4H) 2.40-2.50 (m, 2H) 3.53-3.61 (m, 4H) 4.27 (t, J=8.1 Hz, 4H)

Preparation of 4-azoniaspiro[3,4]octane tetraphenylborate

To a solution of sodium tetraphenylborate (1.90 g) in acetone (8 ml) at 20° C. was added aqueous 4-azoniaspiro[3,4]octane chloride (1.64 ml, prepared as above). The resulting solid was filtered, washed with water (3×10 ml) and dried in a vacuum oven to give 4-azoniaspiro[3,4]octane tetraphenylborate (2.17 g, 90% of theory).

1H NMR Spectrum (400 MHz, DMSO-d$_6$) δ ppm 1.92 (m, 4H) 2.07-2.47 (m, 2H) 3.52-3.55 (m, 4H) 4.23 (t, J=8.1 Hz, 4H), 6.77-6.80 (m, 4H) 6.90-6.94 (m, 8H) 7.15-7.20 (m, 8H)

13C NMR Spectrum (100 MHz, DMSO-d$_6$) δ ppm 14.12 (s, 1C) 20.71 (s, 1C) 62.01 (s, br, 2C) 121.45 (s, 8C) 125.21 (m, 8C) 135.5 (s, 4C) 163.3 (m, 4C)

Preparation of 4-azoniaspiro[3,4]octane bromide 1,3-dibromopropane (287 ml) was heated to 45° C. and pyrrolidine (23.4 ml) added over 4 hours. The mixture was then cooled to room temperature and evaporated to dryness on a is rotary evaporator. To the residual oil was added water (200 ml) and the small organic lower layer separated. The solution was washed with dichloromethane (20 ml). The aqueous layer was basified by the addition of potassium carbonate (42.8 g) and extracted with dichloromethane (2×80 ml). The combined organic extracts were dried over magnesium sulphate and evaporated to dryness on a rotary evaporator. The residue was triturated by the addition of acetone (30 ml) and stirred overnight. The solid was filtered, washed with acetone (30 ml) and dried in a vacuum oven at 40° C.

Yield 3.06 g, 5.7%

1H NMR Spectrum (400 MHz, DMSO-d$_6$) δ ppm 1.90-1.99 (m, 4H) 2.41-2.50 (m, 2H) 3.53-3.66 (m, 4H) 4.30 (t, J=8.1 Hz, 4H)

M$^+$ 112

Preparation of 4-[(4-fluoro-2-methyl-1H-indol-5-yl)oxy]-6-methoxy-7-(3-pyrrolidin-1-ylpropoxy)quinazoline using 4-azoniaspiro[3,4]octane chloride 4-Azoniaspiro[3,4]octane chloride (1.14 g) was added to a mixture of 4-[(4-fluoro-2-methyl-1H-indol-5-yl)oxy]-6-methoxyquinazolin-7-ol (2.5 g), 1-methyl-2-pyrrolidinone (25 ml), methyl tert-butyl ether (1.8 ml) and potassium carbonate (815 mg) at 80° C. After stirring at 80° C. for 3 hours water (27 ml) was added over 40 minutes. The mixture was allowed to cool to 20° C. and left overnight. The mixture was reheated to 60° C. and filtered. The filter cake was washed with 1:1 v/v 1-methyl-2-pyrrolidinone/water (5 ml) and then with water (4×5 ml). The solid was dried in a vacuum oven to give 4-[(4-fluoro-2-methyl-1H-indol-5-yl)oxy]-6-methoxy-7-(3-pyrrolidin-1-ylprpoxy)quinazoline.

Yield 2.29 g at 94.2% w/w, 65.0% of theory

Preparation of 4-[(4-fluoro-2-methyl-1H-indol-5-yl)oxy]-6-methoxy-7-(3-pyrrolidin-1-ylpropoxy)quinazoline using 4-azoniaspiro[3,4]octane bromide To a solution of 4-[(4-fluoro-2-methyl-1H-indol-5-yl)oxy]-6-methoxyquinazolin-7-ol (2.5 g) in 1-methyl-2-pyrrolidinone (25 ml) and methyl tert-butyl ether (1.8 ml) was added potassium carbonate (815 mg). The mixture was degassed by holding under vacuum and letting down with nitrogen. This was carried out five times. The mixture was heated to 80° C. and 4-azoniaspiro[3,4]octane bromide (1.75 g) was added. The mixture was maintained at 80° C. for 3.5 hours. To the hot mixture was added water (27 ml) over 2 hours. The mixture was cooled to 64° C. and the solid filtered. The solid was washed with 1:1 v/v 1-methyl-2-pyrrolidinone/water (5 ml) and then water (4×5 ml). The solid was dried in a vacuum oven to give 4-[(4-fluoro-2-methyl-1H-indol-5-yl)oxy]-6-methoxy-7-(3-pyrrolidin-1-ylprpoxy)quinazoline.

Yield 2.75 g at 94.2% w/w, 78.0% of theoretical

Preparation of 4-[(4-fluoro-2-methyl-1H-indol-5-yl)oxy]-6-methoxy-7-(3-pyrrolidin-1-ylpropoxy)quinazoline using 4-azoniaspiro[3,4]octane hexafluorophosphate The reaction was carried out as for the bromide salt, but using 4-azoniaspiro[3,4]octane hexafluorophosphate (1.99 g).

Yield 2.20 g at 94.2% w/w, 62.4% of theoretical

Example 9

Preparation of 4-[(4-fluoro-2-methyl-1H-indol-5-yl)oxy]-6-methoxyquinazolin-7-ol via hydrogenation of 1-(3-{[7-(benzyloxy)-6-methoxyquinazolin-4-yl]oxy}-2-fluoro-6-nitrophenyl)acetone

Preparation of 1-(3-{[7-(benzyloxy)-6-methoxyquinazolin-4-yl]oxy}-2-fluoro-6-nitrophenyl)acetone 1-(2-Fluoro-3-hydroxy-6-nitrophenyl)-propan-2-one (4.286 g) was suspended in acetonitrile (16 ml) and cooled to −5° C. To the slurry was added aqueous sodium hydroxide (0.93 ml of 46.9% w/w solution). A line wash of acetonitrile (16 ml) was applied.

This cold solution was added to a solution of 7-(benzyloxy)-4-chloro-6-methoxyquinazoline (4.26 g) in anisole (28.8 ml) at 80° C. over 15 minutes. A line wash of acetonitrile (16 ml) was applied. The mixture was heated at 80° C. for 21 hours. The stirrer was stopped and the lower aqueous layer separated. The upper organic layer was washed further with water (6 ml) at 80° C.

The batch was cooled to 20° C. and concentrated under reduced pressure (130 mbar), allowing the batch temperature to reach 100° C., collecting 24 ml of distillate. The batch temperature was adjusted to 65° C. and a solution of water (4 ml) in methanol (28 ml) added. The mixture was cooled to 20° C. and the product filtered. The filter cake was washed with methanol (2×12 ml) and dried in a vacuum oven at overnight to give 1-(3-{[7-(benzyloxy)-6-methoxyquinazolin-4-yl]oxy}-2-fluoro-6-nitrophenyl)acetone (4.543 g, 67% of theory).

1H NMR Spectrum (400 MHz, DMSO-$d_6$) δ ppm 2.29 (s, 3H) 4.00 (s, 3H) 4.27 (s, 2H) 5.37 (s, 2H) 7.38 (m, 1H) 7.44 (m, 2H) 7.53 (m, 2H) 7.56 (s, 1H) 7.62 (s, 1H) 7.77 (dd, J=9.1, 7.8 Hz, 1H) 8.12 (dd, J=9.05, 0.81 Hz, 1H) 8.59 (s, 1H)

Mass Spectrum [M+H]$^+$

Hydrogenation of 1-(3-{[7-(benzyloxy)-6-methoxyquinazolin-4-yl]oxy}-2-fluoro-6-nitrophenyl)acetone to give 4-[(4-fluoro-2-methyl-1H-indol-5-yl)oxy]-6-methoxyquinazolin-7-ol To a solution of 1-(3-{[7-(benzyloxy)-6-methoxyquinazolin-4-yl]oxy}-2-fluoro-6-nitrophenyl)acetone (0.75 g) in 1-methyl-2-pyrrolidinone (7.5 ml) was charged 10% palladium on charcoal catalyst (38.6 mg of approximately 50% water wet paste). The mixture was warmed to 50° C. and hydrogenated under 4 bar atmosphere of hydrogen for 2.75 hours. This gave a solution containing 28% peak area of 4-[(4-fluoro-2-methyl-1H-indol-5-yl)oxy]-6-methoxyquinazolin-7-ol.

Hplc retention time of 4-[(4-fluoro-2-methyl-1H-indol-5-yl)oxy]-6-methoxyquinazolin-7-ol 12.36 mins. This was identical to the retention time of 4-[(4-fluoro-2-methyl-1H-indol-5-yl)oxy]-6-methoxyquinazolin-7-ol as prepared in Example 6.

Hplc method: Column Betabasic C18 3.5 μm, 150 mm×4.6 mm id. Temperature 30° C. Injection volume 10 μl. UV 260 nm, response>0.1 min (2 sec). Flow rate 1.0 ml/min. Data Collection 17 min. Run time 21 min Eluent A Water; Eluent B acetonitrile; Eluent C 1% aqueous trifluroacetic acid.

|  | Time (min) | % A | % B | % C |
|---|---|---|---|---|
| Gradient: | 0 | 70 | 15 | 15 |
|  | 5 | 55 | 30 | 15 |
|  | 9 | 55 | 30 | 15 |
|  | 14 | 0 | 85 | 15 |
|  | 17 | 0 | 85 | 15 |

[M + H]$^+$ 340

The invention claimed is:
1. A process for the manufacture of a compound of Formula II

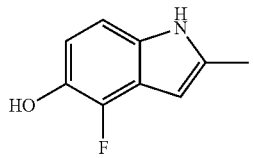

II the process comprising the steps of:
(a) in the presence of a solvent, reacting a compound of Formula III:

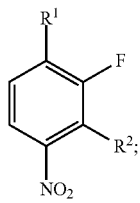

III wherein $R^1$ and $R^2$ are independently selected from the group consisting of chlorine, bromine, fluorine, iodine, triflyl and tosyl;
with an ester of Formula IV

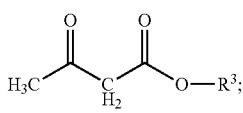

IV wherein $R^3$ is
$C_{1-6}$alkyl or benzyl;
to form a compound of Formula V:

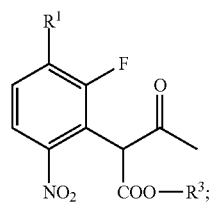

V (b) in the presence of an arylalkyl ammonium salt or a tetraalkyl ammonium salt, reacting a compound of Formula V with hydroxide ion to form a compound of Formula VI

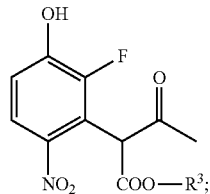

VI (c) in the presence of an acid, decarboxylating a compound of Formula VI to form a compound of Formula VII;

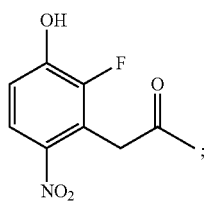

VII and
(d) reducing the compound of Formula VII to form the compound of Formula II.

2. The process according to claim 1, wherein step (a) is conducted in a solvent selected from the group consisting of toluene, trimethylbenzene and xylene.

3. The process according to claim 2, wherein the solvent is toluene.

4. The process according to claim 2, wherein the solvent is trimethylbenzene.

5. The process according to claim 2, wherein the solvent is xylene.

6. The process according to claim 1, wherein $R^1$ and $R^2$ are both fluorine.

7. The process according to claim 1, wherein step (b) is carried out in the presence of trimethyl benzyl ammonium hydroxide.

8. The process according to claim 1, wherein $R^1$ and $R^2$ are independently selected from the group consisting of chlorine, bromine, fluorine and iodine.

9. The process according to claim 1, wherein $R^1$ and $R^2$ are independently selected from the group consisting of triflyl and tosyl.

10. The process according to claim 1, wherein $R^3$ is $C_{1-6}$alkyl.

11. The process according to claim 1, wherein $R^3$ is benzyl.

12. The process according to claim 1, wherein step (b) is carried out in the presence of an arylalkyl ammonium salt.

13. The process according to claim 1, wherein step (b) is carried out in the presence of a tetraalkyl ammonium salt.

* * * * *